(12) United States Patent
Demmer et al.

(10) Patent No.: US 9,399,139 B2
(45) Date of Patent: Jul. 26, 2016

(54) SYSTEM AND METHOD FOR DUAL-CHAMBER PACING

(71) Applicant: Medtronic, Inc., Minneapolis, MN (US)

(72) Inventors: Wade M. Demmer, Coon Rapids, MN (US); Saul E. Greenhut, Aurora, CO (US); Todd J. Sheldon, North Oaks, MN (US); David A. Anderson, Stanchfield, MN (US); Karen J. Kleckner, New Brighton, MN (US); James K. Carney, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/578,656

(22) Filed: Dec. 22, 2014

(65) Prior Publication Data
US 2016/0067487 A1    Mar. 10, 2016

Related U.S. Application Data

(60) Provisional application No. 62/047,418, filed on Sep. 8, 2014, provisional application No. 62/068,377, filed on Oct. 24, 2014.

(51) Int. Cl.
*A61N 1/00* (2006.01)
*A61N 1/365* (2006.01)
(Continued)

(52) U.S. Cl.
CPC .............. *A61N 1/365* (2013.01); *A61N 1/0573* (2013.01); *A61N 1/368* (2013.01); *A61N 1/3627* (2013.01); *A61N 1/3684* (2013.01); *A61N 1/36507* (2013.01); *A61N 1/36514* (2013.01); *A61N 1/36542* (2013.01); *A61N 1/36578* (2013.01); *A61N 1/36585* (2013.01); *A61N 1/36592* (2013.01); *A61N 1/3756* (2013.01);
(Continued)

(58) Field of Classification Search
CPC . A61N 1/3682; A61N 1/365; A61N 1/36578; A61N 1/368
See application file for complete search history.

(56) References Cited

U.S. PATENT DOCUMENTS

| 4,967,746 A | 11/1990 | Vandegriff |
|---|---|---|
| 5,507,782 A | 4/1996 | Kieval et al. |

(Continued)

FOREIGN PATENT DOCUMENTS

| EP | 147820 | 7/1985 |
|---|---|---|
| EP | 526798 | 2/1993 |

(Continued)

OTHER PUBLICATIONS

Non-Final Office action mailed Nov. 10, 2015 for U.S. Appl. No. 14/578,698, 15 pages.

(Continued)

*Primary Examiner* — Robert N Wieland
(74) *Attorney, Agent, or Firm* — Evans M. Mburu

(57) ABSTRACT

A medical device system including an pacemaker implantable in a chamber of a patient's heart is configured to sense near field events from a cardiac electrical signal, establish a lower rate interval to control a rate of delivery of pacing pulses and schedule a first pacing pulse by starting a pacing escape interval set equal to the lower rate interval. The pacemaker withholds the scheduled pacing pulse in response to sensing a near-field event during the pacing escape interval and schedules a next pacing pulse to be delivered at the lower rate interval from a time that the pacing escape interval is scheduled to expire.

28 Claims, 13 Drawing Sheets

(51) Int. Cl.
  *A61N 1/368* (2006.01)
  *A61N 1/375* (2006.01)
  *A61N 1/05* (2006.01)
  *A61N 1/362* (2006.01)
  *A61N 1/372* (2006.01)

(52) U.S. Cl.
  CPC ........... *A61N1/37205* (2013.01); *A61N 1/3688* (2013.01); *A61N 1/36528* (2013.01)

(56) References Cited

U.S. PATENT DOCUMENTS

| | | |
|---|---|---|
| 5,683,432 A | 11/1997 | Goedeke et al. |
| 5,725,561 A | 3/1998 | Stroebel et al. |
| 5,928,271 A | 7/1999 | Hess et al. |
| 6,920,356 B2 | 7/2005 | Armstrong et al. |
| 7,031,772 B2 | 4/2006 | Condie et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 2002/0082649 A1 | 6/2002 | Stahmann et al. |
| 2007/0088405 A1 | 4/2007 | Jacobson |
| 2007/0293897 A1* | 12/2007 | Sheldon ................. A61N 1/368 607/9 |
| 2012/0172892 A1 | 7/2012 | Grubac et al. |
| 2013/0035748 A1 | 2/2013 | Bonner et al. |
| 2013/0116738 A1 | 5/2013 | Samade et al. |
| 2013/0123872 A1 | 5/2013 | Bornzin et al. |
| 2014/0121720 A1 | 5/2014 | Bonner et al. |

FOREIGN PATENT DOCUMENTS

| | | |
|---|---|---|
| EP | 0559847 | 3/1993 |
| WO | 9216258 | 10/1992 |
| WO | 2006065394 A1 | 6/2006 |
| WO | 2013016374 | 1/2013 |
| WO | 2013096015 | 6/2013 |
| WO | 2014070473 A1 | 5/2014 |

OTHER PUBLICATIONS

Response filed on Feb. 10, 2016 in U.S. Appl. No. 14/578,698 in response to Nov. 10, 2015 office action, 13 pages.
(PCT/US2015/043904) PCT Notification of Transmittal of the International Search Report and the Written Opinion of the International Searching Authority, mailed Oct. 20, 2015, 11 pages.
(PCT/US2015/042334) PCT Notification of Transmittal of the International Search Report and the Written Opinion of the International Searching Authority, mailed Oct. 21, 2015, 10 pages.

* cited by examiner

SYSTEM AND METHOD FOR DUAL-CHAMBER PACING

CROSS-REFERENCE TO RELATED APPLICATIONS

This application claims the benefit of U.S. Provisional Application Nos. 62/047,418, filed on Sep. 8, 2014 and 62/068,377, filed on Oct. 24, 2014. The disclosure of the above applications are incorporated herein by reference in its entirety.

TECHNICAL FIELD

The disclosure relates to an implantable medical device system and associated method for controlling intracardiac pacemakers to deliver coordinated dual chamber pacing to a patient's heart.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular pacing may adequately address some patient conditions, other conditions may require atrial and ventricular pacing, commonly referred to a dual chamber pacing, in order to maintain a regular heart rhythm.

SUMMARY

In general, the disclosure is directed to implantable medical device (IMD) systems that include an atrial intracardiac pacemaker and techniques for controlling pacing pulses delivered by the atrial intracardiac pacemaker to deliver coordinated dual chamber pacing. The IMD system may include a ventricular intracardiac pacemaker for pacing in a ventricular chamber. An intracardiac atrial pacemaker operating in accordance with the techniques disclosed herein controls atrial pacing escape intervals in response to atrial events and far-field ventricular events that are sensed by the atrial intracardiac pacemaker. The atrial intracardiac pacemaker delivers atrial pacing pulses that are coordinated with ventricular events without requiring sensing of atrial events by a ventricular intracardiac pacemaker when present.

In one example, the disclosure provides an implantable medical device (IMD) system comprising a pacemaker implantable in a chamber of a heart of a patient. The pacemaker comprises a sensing module configured to receive a cardiac electrical signal and sense near field events in the heart chamber from the cardiac electrical signal, a pulse generator configured to generate and deliver pacing pulses to the heart chamber via a pair of electrodes, and a control module coupled to the sensing module and the pulse generator. The control module is configured to establish a lower rate interval to control a rate of delivery of the pacing pulses, schedule a first pacing pulse to be delivered by the pulse generator by starting a pacing escape interval equal to the lower rate interval, withhold the scheduled pacing pulse in response to the sensing module sensing a near-field event during the pacing escape interval, and schedule a next pacing pulse to be delivered at the lower rate interval from a time that the pacing escape interval is scheduled to expire.

In another example, the disclosure provides a method comprising sensing near field events in a chamber of a patient's heart from a cardiac electrical signal received by a sensing module of a pacemaker implantable in the heart chamber, establishing by the pacemaker a lower rate interval to control a rate of delivery of pacing pulses, scheduling a first pacing pulse by starting a pacing escape interval set equal to the lower rate interval, withholding the scheduled pacing pulse in response to sensing a near-field event during the pacing escape interval; and scheduling a next pacing pulse to be delivered at the lower rate interval from a time that the pacing escape interval is scheduled to expire.

In yet another example, the disclosure provides a non-transitory, computer-readable storage medium comprising a set of instructions which, when executed by a control module of a pacemaker implantable in a chamber of a patient's heart, cause the pacemaker to sense near field events from a cardiac electrical signal, establish a lower rate interval to control a rate of delivery of pacing pulses, schedule a first pacing pulse by starting a pacing escape interval set equal to the lower rate interval, withholding the scheduled pacing pulse in response to sensing a near-field event during the pacing escape interval; and scheduling a next pacing pulse to be delivered at the lower rate interval from a time that the pacing escape interval is scheduled to expire.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

Figure 1:
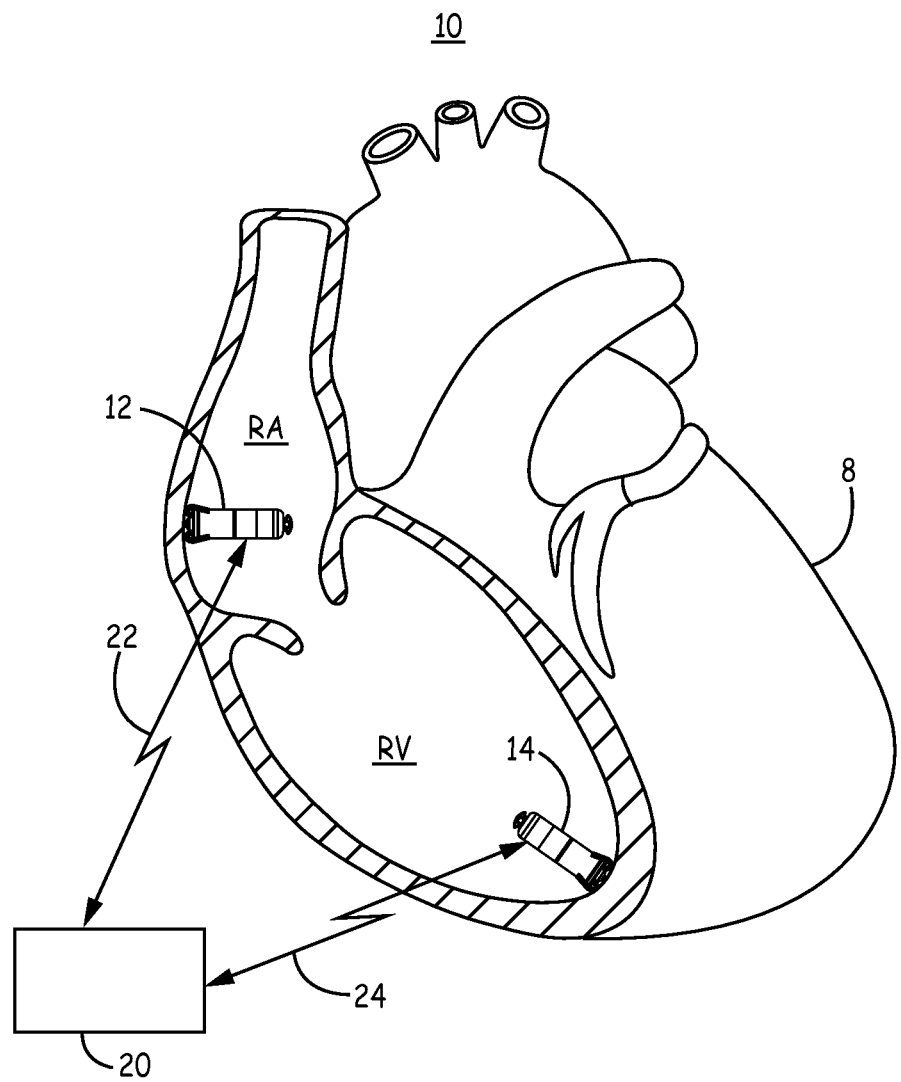
FIG. 1 is a conceptual diagram illustrating an intracardiac pacing system that may be used to sense cardiac electrical signals and provide therapy to a patient's heart.

An implantable medical device (IMD) system is disclosed herein that includes an intracardiac pacemaker configured to be implanted wholly in a chamber of the patient's heart. In various examples, the IMD system includes an atrial intracardiac pacemaker and a ventricular intracardiac pacemaker that do not require transvenous leads but are enabled to provide coordinated atrial and ventricular pacing without wireless or wired communication signals between the two intracardiac pacemakers. An atrial intracardiac pacemaker included in the system includes a control module that monitors ventricular events and controls atrial pacing pulse delivery based on sensed ventricular events (or lack thereof) to promote atrial-ventricular synchrony.

In past practice, a dual chamber pacemaker positioned in an implant pocket and coupled to transvenous atrial and ventricular leads may be programmed to deliver only atrial pacing (AAI(R)), only ventricular pacing (VVI(R)) or both (DDD(R)) according to patient need. The dual chamber pacemaker is able to control the delivery of pacing pulses in both atrial and ventricular chambers because the pacemaker will receive cardiac event signals from both atrial and ventricular chambers via correspondingly placed sensing electrodes and control when a pacing pulse is delivered in both chambers relative to the sensed events using the electrodes positioned in both chambers. In other words, the dual chamber pacemaker "knows" when both sensed and paced events have occurred in both atrial and ventricular pacing channels since all sensing and pacing control is happening in the one device, i.e., the dual chamber pacemaker.

Intracardiac pacemakers adapted to be implanted wholly within a heart chamber eliminate the need for transvenous, intracardiac leads. Complications due to infection associated with a lead extending from a subcutaneous pacemaker pocket transvenously into the heart can be eliminated. Other complications such as "Twiddler's syndrome", lead fracture or poor connection of the lead to the pacemaker are eliminated in the use of an intracardiac pacemaker.

An intracardiac pacemaker can operate in a single chamber mode, e.g., AAI or VVI, by delivering pacing pulses and inhibiting pacing when an intrinsic event is sensed in the chamber that the pacemaker is implanted in. While some patients may require only single chamber pacing and sensing, patients having AV conduction defects may require a pacing system capable of a coordinated dual chamber pacing mode to provide pacing in the ventricle that is coordinated with atrial events. An atrial intracardiac pacemaker and associated techniques are disclosed herein which provide ventricular-synchronized atrial pacing to promote atrial pacing at a target atrioventricular (AV) interval relative to ventricular events, which may include ventricular pacing pulses being delivered by an intracardiac ventricular pacemaker operating independently of the atrial intracardiac pacemaker. Maintaining a target AV interval is important for maintaining proper filling of the ventricles and promoting optimal cardiac hemodynamic function in patient's having intrinsic AV conduction defects.

FIG. 1 is a conceptual diagram illustrating an intracardiac pacing system 10 that may be used to sense cardiac electrical signals and provide therapy to a patient's heart 8. IMD system 10 includes a right atrial (RA) intracardiac pacemaker 12 and a right ventricular (RV) intracardiac pacemaker 14. Pacemakers 12 and 14 are transcatheter intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible. In some examples, a RA intracardiac pacemaker 12 and a LV intracardiac pacemaker are implanted for delivering coordinated atrial and ventricular pacing using the techniques disclosed herein.

Pacemakers 12 and 14 are reduced in size and may be generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using one or more housing based electrodes and deliver RV pacing pulses.

The RA pacemaker 12 and the RV pacemaker 14 are configured to control the delivery of pacing pulses to the respective atrial and ventricular chambers in a manner that promotes maintaining a target AV interval between atrial events (e.g., P-waves or atrial pacing pulses) and ventricular events (e.g., R-waves or ventricular pacing pulses). A target AV interval may be a programmed value selected by a clinician. A target AV interval may be identified as being hemodynamically optimal for a given patient based on clinical testing or assessments. Each of the RA pacemaker 12 and RV pacemaker 14 include a control module that controls functions performed by the respective pacemaker. The control module of the RA pacemaker 12 is configured to automatically adjust atrial pacing escape intervals to increase the likelihood that an atrial pacing pulse is delivered at a target AV interval prior to an RV event. The control module of the RV pacemaker 14 may be configured to control ventricular pacing pulses to minimize ventricular pacing when intrinsic AV conduction is intact, but may be operating independently of RA pacemaker 12 in that RV pacemaker 14 may not be configured to sense atrial events. Both the RA pacemaker control module and the RV pacemaker control module may be configured to adjust pacing timing intervals based on a sensor signal correlated to the metabolic demand of the patient to provide rate responsive pacing.

Pacemaker 12 and 14 are each capable of bidirectional wireless communication with an external device 20. External device 20 may be a programmer used by a clinician or other user in a medical facility, a home monitor located in a patient's home, or a handheld device. Aspects of external device 20 may generally correspond to the external programming/monitoring unit disclosed in U.S. Pat. No. 5,507,782 (Kieval, et al.), hereby incorporated herein by reference in its entirety.

External device 20 may be configured to establish a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat. No. 5,683,432 (Goedeke, et al.), hereby incorporated herein by reference in its entirety.

External device 20 may be used for retrieving data from pacemakers 12 and 14 and for sending data to pacemakers 12 and 14. Examples of retrieved data include physiological signals such as RA or RV EGM signals, therapy delivery data such as a history of pacing frequency, results of device diagnostic testing, current operating control parameters or other data stored by the pacemaker. Data sent to pacemakers 12 and 14 may include programmable control parameters used by the pacemakers 12 and 14 to control sensing and pacing functions.

RA pacemaker 12 and RV pacemaker 14 may or may not be configured to communicate directly with each other. For example, neither RA pacemaker 12 nor RV pacemaker 14 may be configured to initiate an RF communication session with the other device. Both pacemakers 12, 14 may be configured to periodically "listen" for a valid "wake up" telemetry signal from external device 20 and power up its own telemetry module to establish a communication link 22 or 24 in response to a valid RF telemetry signal (or go back to "sleep" if no valid telemetry signal is received). However, pacemakers 12 and 14 may not be configured to transmit a "wake up" signal to the other pacemaker to initiate a communication session. In other examples, the pacemakers 12 and 14 may be configured to communicate with each other, but, in order to conserve battery life of the intracardiac pacemakers, telemetry communication may be minimized. As such, communication does not occur on a beat-by-beat basis between the RA pacemaker 12 and RV pacemaker 14 for communicating when the other pacemaker is sensing cardiac events or when it is delivering pacing pulses.

In accordance with techniques disclosed herein, RA pacemaker 12 is configured to sense far-field (FF) ventricular events from the RA EGM signal. FF ventricular events may include ventricular pacing pulses delivered by RV pacemaker 14 and/or R-waves, e.g., associated with pacing evoked responses, intrinsically conducted ventricular depolarizations, and premature ventricular contractions. In some examples, RA pacemaker 12 includes a sensing module configured to sense FF ventricular events from heart sounds using an acoustical sensor.

RV pacemaker 14 may or may not be configured to sense far-field P-waves and FF atrial pacing pulses from the RV EGM signal. In some examples, RV pacemaker 14 is not configured to sense atrial events. In other examples, RV pacemaker 14 is configured to sense atrial events and may include a conductor extending from the pacemaker housing to increase sensing electrode distance to improve FF atrial event sensing.

Figure 2A:
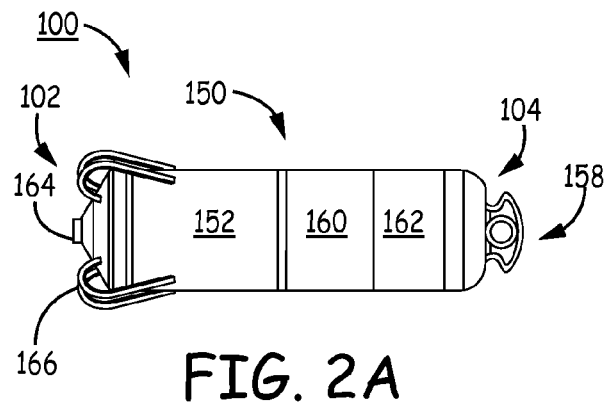
FIG. 2A is a conceptual diagram of an intracardiac pacemaker.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. Relatively greater inter-electrode spacing will increase the likelihood of sensing FF signals that may be used by the pacemaker 100 for sensing events in another heart chamber. For example, an increased inter-electrode spacing between electrodes 162 and 164 when pacemaker 100 is used as an RV pacemaker 14 may improve reliable sensing of FF P-waves.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of active fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 is located at the proximal end 104 of pacemaker 100 and is configured to connect to a delivery device, such as a catheter, used to position pacemaker 100 at an implant location during an implantation procedure, for example within a heart chamber.

A reduced size of pacemaker 100 enables implantation wholly within a heart chamber. In FIG. 1, RA pacemaker 12 and RV pacemaker 14 may have different dimensions. For example, RA pacemaker 12 may be smaller in volume than pacemaker 14, e.g., by reducing battery size, to accommodate implantation in the smaller heart chamber. As such, it is recognized that pacemaker 100 may be adapted in size, shape, electrode location or other physical characteristics according to the heart chamber in which it will be implanted.

Figure 2B:
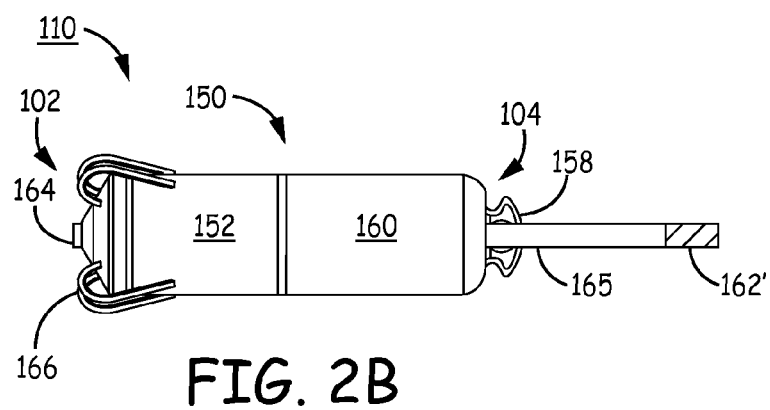
FIGS. 2B and 2C are conceptual diagrams of alternative embodiments of an intracardiac pacemaker.

FIG. 2B is a conceptual diagram of an alternative embodiment of an intracardiac pacemaker 110. Pacemaker 110 includes a housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an extender 165. As such, instead of carrying a pair of electrodes along the housing 150, which limits the maximum possible inter-electrode spacing, an extender 165 may be coupled to the housing 150 using necessary electrical feedthroughs for positioning an electrode 162' at an increased inter-electrode distance from distal tip electrode 164.

For examples of an intracardiac pacemaker having increased inter-electrode spacing between electrodes, reference is made to commonly-assigned, pre-grant U.S. Publication No. 2013/0035748 (Bonner, et al.) and U.S. Patent Application Ser. No. 62/025,690, filed on Jul. 17, 2014, both of which are incorporated herein by reference their entirety.

Figure 2C:
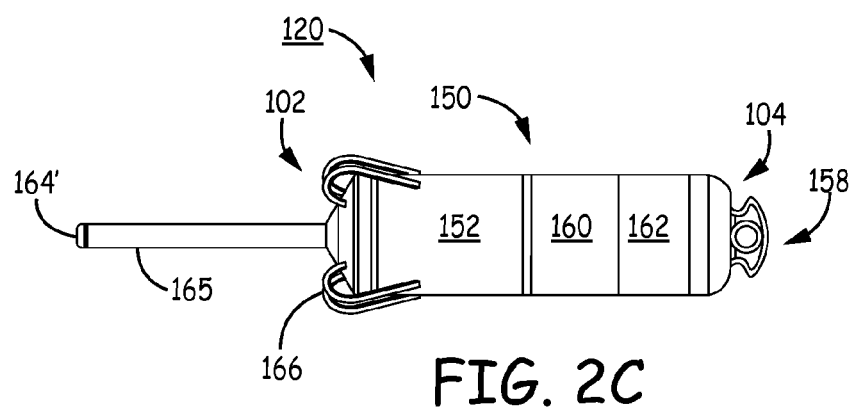

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 shown in FIGS. 2B and 2C is an insulated electrical conductor that electrically couples electrode 162' (FIG. 2B) or electrode 164' (FIG. 2C) to pacemaker circuitry via an electrical feedthrough crossing housing 150. Pacemaker 120 having an insulated, electrically conductive extender 165 for increasing the inter-electrode spacing may correspond generally to the implantable device and flexible conductor disclosed in the above incorporated U.S. Publication No. 2013/0035748 (Bonner, et al.).

Figure 3:
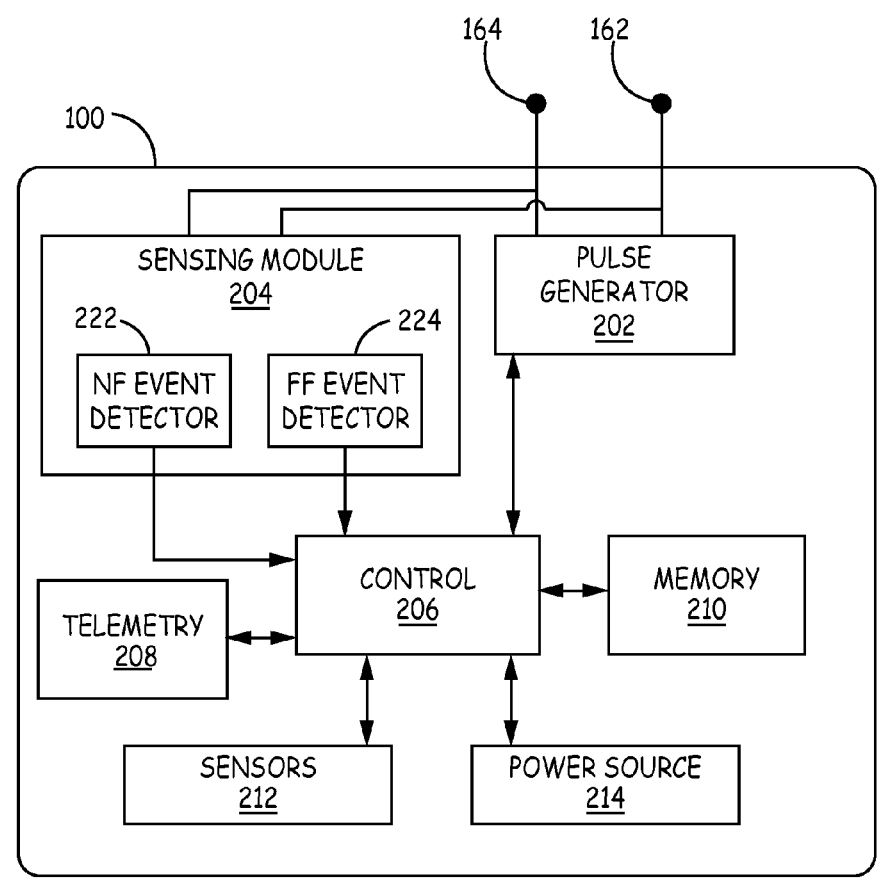
FIG. 3 is a functional block diagram of an example configuration of the intracardiac pacemaker shown in FIG. 2A.

FIG. 3 is a functional block diagram of an example configuration of pacemaker 100 shown in FIG. 2A. Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 will include similar modules as represented by the pacemaker 100 shown in FIG. 3; however it is understood that the modules are configured differently as needed to perform the functionality of the separate RA and RV pacemakers 12 and 14 as disclosed herein.

For example, when pacemaker 100 is a RA pacemaker 12, control module 206 is configured to set various atrial pacing escape intervals used to control delivery of atrial pacing pulses as disclosed herein. When pacemaker 100 is embodied as RV pacemaker 14, control module 206 is configured to set ventricular pacing escape intervals to control delivery of RV pacing pulses according to techniques disclosed herein. Adaptations of the hardware, firmware or software of the various modules of pacemaker 100 necessary to meet the described functionality of the intracardiac pacemakers positioned in different heart chambers as disclosed herein is understood to be included in the various modules of pacemaker 100 according to the intended implant location.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, e.g., as controlled by a pacing escape interval timer included in a pace timing and control circuit in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control circuit included in control module 206 includes an escape interval timer or counter that is set to various pacing escape intervals used for controlling the timing of pacing pulses relative to a paced or sensed event. Upon expiration of a pacing escape interval, a pacing pulse is delivered. If a cardiac event is sensed during the pacing timing interval by sensing module 204, the scheduled pacing pulse may be inhibited, and the pacing escape interval may be reset to a new time interval. Control of pacing escape intervals by control module 206 are described below in conjunction with the various flow charts and timing diagrams presented herein.

Sensing module 204 includes cardiac event detectors 222 and 224 for receiving cardiac EGM signals developed across electrodes 162 and 164. A cardiac event is sensed by sensing module 204 when the EGM signal crosses a sensing threshold of a cardiac event detector 222 or 224 in some examples. The sensing threshold may be an auto-adjusting sensing threshold that may be initially set based on the amplitude of a sensed event and decays at a predetermined decay rate thereafter. In response to a sensing threshold crossing, sensing module 204 passes a sensed event signal to control module 206.

Sensing module 204 may include a near-field (NF) event detector 222 and a far-field (FF) event detector 224. NF cardiac events are events that occur in the heart chamber where the electrodes 162 and 164 are located. FF cardiac events are events that occur in a different heart chamber than the heart chamber where electrodes 162 and 164 are located.

The NF cardiac event detector 222 of RA pacemaker 12 may be programmed or configured to operate using a sensing threshold appropriate for sensing P-waves attendant to the depolarization of the atria. The NF cardiac event detector 222 of RV pacemaker 14 may be programmed or configured to operate using a sensing threshold appropriate for sensing R-waves attendant to the depolarization of the ventricles. NF cardiac event detector 222 produces a sensed event signal provided to control module 206 in response to sensing a NF event, i.e., a P-wave by RA pacemaker 12 or an R-wave by RV pacemaker 14.

The terms "sensed cardiac events" or "sensed events" as used herein refer to events sensed by sensing module 204 in response to the EGM signal crossing a sensing threshold, which may be an amplitude threshold, a frequency threshold, a slew rate threshold, or any combination thereof. Sensed cardiac events may include intrinsic events and evoked events. Evoked events include P-waves in the atria or R-waves in the ventricle caused by a pacing pulse delivered in the respective heart chamber. Intrinsic events are events arising in the heart in the absence of a pacing pulse delivered in the heart chamber in which the intrinsic event is sensed. Intrinsic events include intrinsic P-waves, such as sinus P-waves originating from the sino-atrial node of the heart, and intrinsic R-waves, such as sinus R-waves conducted through the heart's normal conduction pathway to the ventricles from the atria via the atrioventricular node. Intrinsic events can also include non-sinus intrinsic events, such as premature atrial contractions (PACs) or premature ventricular contractions (PVCs) that arise intrinsically from the heart but are ectopic in origin.

FF event detector 224 may be configured to sense FF ventricular events when pacemaker 100 is embodied as RA pacemaker 12. A FF ventricular event sensing threshold may be used by FF event detector 224 for sensing FF ventricular events. FF event detector 224 produces a FF sensed event signal that is passed to control module 206 in response to sensing a FF event. FF ventricular events sensed by FF event detector 224 may include ventricular pacing pulses delivered by RV pacemaker 14 and/or R-waves, intrinsic or evoked. The FF event detector 224 may or may not be configured to discriminate between sensed FF ventricular events that are pacing pulses and sensed FF ventricular events that are R-waves.

As used herein, "FF ventricular events" may refer collectively to both ventricular pacing pulses and ventricular R-waves that are sensed by FF event detector 224 in RA pacemaker 12, which may produce FF ventricular event sense signals in response to the EGM signal meeting ventricular event sensing criteria that may include sensing of both ventricular pacing pulses and R-waves non-discriminately. In other examples, the FF event detector 224 may be configured to discriminately sense ventricular pacing pulse and/or ventricular R-waves and provide different sense event signals to control module 206 in response to each.

In some examples, RV pacemaker 14 does not include a FF event detector 224 configured to sense FF atrial events. In this case, RV pacemaker 14 is configured for single chamber sensing of R-waves in the ventricle. FF P-waves are relatively small amplitude signals compared to NF R-waves and may be difficult to distinguish from baseline noise on the ventricular EGM signal. As described in conjunction with the flow charts and timing diagrams disclosed herein, coordinated atrial and ventricular pacing may be provided by RA pacemaker 12 and RV pacemaker 14 without requiring RV pacemaker 14 to sense FF atrial events.

In other examples, RV pacemaker may include a FF event detector 224 configured to sense FF atrial pacing pulses and/or FF atrial P-waves, intrinsic or evoked. The inter-electrode spacing of sensing electrodes 162 and 164 may be increased to enhance sensing of small amplitude FF P-waves by FF event detector 224, e.g., by using an extender as shown in FIG. 2B and FIG. 2C.

When available, FF atrial event signals produced by FF event detector 224 in RV pacemaker 14 may be used by control module 206 of RV pacemaker 14 to deliver atrial-synchronized ventricular pacing. FF atrial events, however, may be undersensed by RV pacemaker 14. Using the techniques disclosed herein, RA pacemaker 14 is configured to deliver atrial pacing pulses in a manner that maintains coordinated atrial and ventricular activity even in the absence or loss of FF atrial event sensing by RV pacemaker 14.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EE-PROM), flash memory, or other digital media with the sole exception being a transitory propagating signal. Memory 210 may store timing intervals, counters, or other data used by control module 206 to control the delivery of pacing pulses by pulse generator 202, e.g., by setting a pacing escape interval timer included in control module 206, according to the techniques disclosed herein.

Pacemaker 100 may further include one or more physiological sensors 212 used for monitoring the patient. In some examples, physiological sensors 212 include at least one physiological sensor producing a signal indicative of the metabolic demand of the patient. The signal indicative of the patient's metabolic demand is used by control module 206 for determining a sensor indicated pacing rate to control a pacing rate that meets the patient's metabolic demand. For example, sensors 212 may include an accelerometer for producing a patient activity signal passed to control module 206. An accelerometer included in sensors 212 may be embodied as a piezoelectric crystal for producing a signal correlated to patient body motion. The use of an accelerometer in an intracardiac device for obtaining a patient activity signal is generally disclosed in U.S. patent application Ser. No. 14/174,514 filed on Feb. 6, 2014 (Nikolski, et al.), incorporated herein by reference in its entirety.

The accelerometer signal is used by the control module 206 to determine a sensor-indicated rate (SIR) used to establish a temporary lower rate interval. The control module 206 sets the pacing escape interval based on the established lower rate interval for controlling the pacing rate to meet the metabolic demand of the patient. RA pacemaker 12 may initially set the atrial pacing escape interval timer included in control module 206 to a lower rate interval corresponding to a programmed base pacing rate to provide bradycardia pacing. The lower rate interval may be shortened from the base lower rate interval automatically to provide atrial rate responsive pacing according to the sensor indicated rate determined from the physiological sensor signal and indicative of the patient's metabolic demand, e.g., a patient activity signal from an accelerometer included in sensors 212. Similarly, sensors 212 included in RV pacemaker 14 may include a physiological sensor producing a signal indicative of the patient's metabolic demand, and the control module 206 may establish a ventricular lower rate interval in response to determining a sensor indicated rate based on the physiological signal.

RA pacemaker 12 and RV pacemaker 14 may use the same or different physiological sensors and/or algorithms for producing a signal indicative of the patient's metabolic demand, determining a sensor indicated pacing rate, and establishing a lower rate interval based on the sensor indicated pacing rate for controlling rate responsive pacing in the respective atrial and ventricular chambers. The use of a patient activity signal for providing rate-responsive pacing is generally disclosed in U.S. Pat. No. 7,031,772 (Condie, et al.), incorporated herein by reference in its entirety.

A physiological signal produced by sensors 212 may additionally or alternatively be used by sensing module 204 and/or control module 206 to detect mechanical activity of the patient's heart, such as motion of a heart chamber or heart sounds. For example, when pacemaker 100 is positioned in the RA as the RA pacemaker 12, a signal artifact on an accelerometer signal due to ventricular contraction at the onset of the ventricular systolic ejection phase, may be identified as a FF ventricular event and used as a surrogate for sensing electrical FF ventricular events by FF event detectors 224.

In other examples, an acoustical sensor may be included in sensors 212 for producing a signal comprising heart sound signals. Sensing module 204 may be configured to sense heart sounds from the acoustical signal as evidence of far field ventricular events. RA pacemaker 12 may include an acoustical sensor for use in sensing heart sounds and providing control module 206 with a FF ventricular event sense signal indicating a mechanical ventricular event has occurred. For example, S1 heart sounds may be sensed as a mechanical surrogate for the electrical sensing of ventricular pacing pulses or R-waves.

In some examples RA pacemaker 12 may be configured to sense both electrical FF ventricular events and mechanical FF ventricular events. For example, the S1 heart sound may be used to confirm an electrical FF ventricular sense signal when the S1 heart sound is detected within a predetermined time interval following an electrical FF ventricular event. In another example, providing redundancy of sensing FF ventricular events may avoid undersensing of ventricular events. A mechanical FF ventricular event may be sensed based on detection of the S1 heart sound and used to set an atrial pacing escape interval even if an electrical FF ventricular event was undersensed by FF event detector 224.

Whether control module 206 receives a signal from sensors 212 based on FF mechanical ventricular events or from sensing module 204 based on FF electrical ventricular events, control module 206 of the RA pacemaker 12 may use a FF ventricular event signal to set atrial pacing escape intervals to achieve atrial pacing that is coordinated with ventricular events. When RA pacemaker control module 206 is configured to set an atrial pacing escape interval timer to coordinate atrial pacing pulses with ventricular events based on mechanical FF ventricular events, the time intervals used by the control module 206 to set the atrial escape interval timer are adjusted accordingly to account for relative differences in timing of electrical and mechanical ventricular events.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data via a radio frequency (RF) communication link. RF communication with external device 20 (FIG. 1), may occur in the Medical Implant Communication Service (MICS) band, the Medical Data Service (MEDS) band, or other frequency bands, including, but not limited to a 2.4 GHz industrial, scientific and medical (ISM) band for Bluetooth and IEEE 802.11 b/g/n standards. Telemetry module 208 may be capable of bi-directional communication with external device 20 over a wide range of distances, e.g., up to approximately 10 meters. In other examples, telemetry communication may require the use of a programming head placed in proximity of pacemaker 100 to facilitate data transfer.

Figure 4:
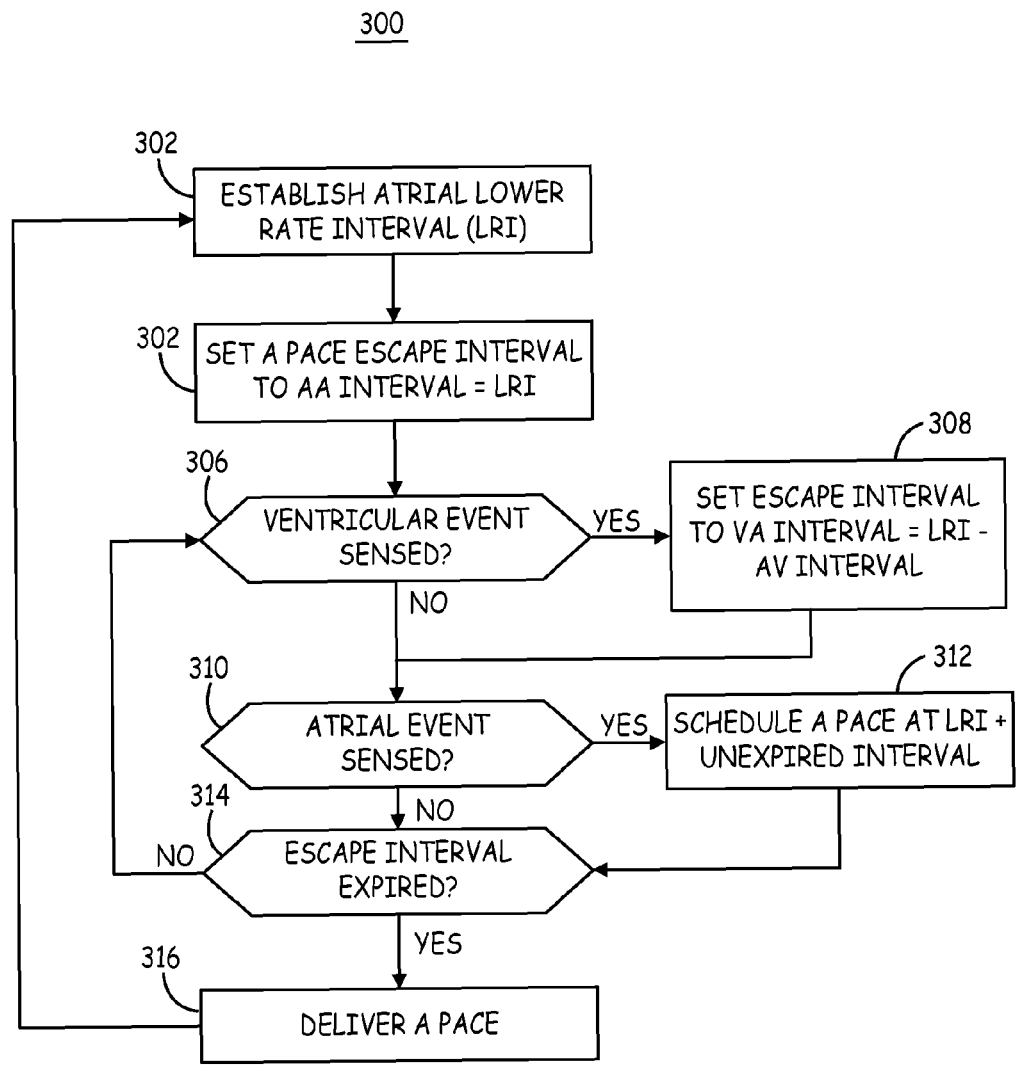
FIG. 4 is a flow chart of a method for controlling atrial pacing pulse delivery by an atrial intracardiac pacemaker.

FIG. 4 is a flow chart 300 of a method for controlling atrial pacing pulse delivery by RA pacemaker 12. Flow chart 300 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the pacemaker 100 and by the particular detection and therapy delivery methodologies employed by the pacemaker 100. Providing software, hardware, and/or firmware to accomplish the described functionality in the context of any modern pacemaker system, given the disclosure herein, is within the abilities of one of skill in the art. Methods described in conjunction with flow charts presented herein may be implemented in a computer-readable medium that includes instructions for causing a programmable processor to carry out the methods described. The instructions may be implemented as one or more software modules, which may be executed by themselves or in combination with other software.

At block 302 an atrial lower rate interval (LRI) is established by the control module 206 of RA pacemaker 12. The LRI may initially be established as a programmed base rate for providing bradycardia pacing. For example, a LRI may initially be 1,000 ms corresponding to a programmed base rate of 60 bpm. A base rate LRI may be set to provide bradycardia pacing in the range of 40 to 70 bpm. The LRI established at block 302 may be adjusted from the programmed base rate according to a sensor-indicated rate determined from a physiological signal indicative of the patient's metabolic demand if rate responsive pacing is enabled. Accordingly, the LRI established at block 302 may be a sensor indicated rate interval, which is sometimes referred to as a "temporary LRI," that is shorter than the base pacing rate interval. The SIR interval is shorter than the base pacing rate interval if an activity sensor signal or other indicator of metabolic demand indicates a higher pacing rate is needed.

As described in greater detail below, the LRI may additionally be adjusted from a (SIR) interval to equalize the atrial rate and a ventricular rate determined from FF ventricular events sensed by RA pacemaker 12. The LRI established at block 302 may therefore be an interval set based on a sensor-indicated rate and a FF ventricular event rate. In this way, the atrial LRI is adjusted at block 302 in response to the physiological sensor-indicated rate and the FF ventricular event rate to match the atrial pacing rate to both the patient's metabolic demand and the ventricular rate when the ventricular rate is most likely a rate-responsive paced ventricular rate and not a ventricular tachyarrhythmia as further described in conjunction with the flow chart of FIG. 7.

At block 304, an atrial pacing escape interval is set to an AA pacing interval equal to the LRI established at block 302. An escape interval timer set to the atrial pacing escape interval is started at block 304 in response to an initial atrial pacing pulse to control the timing of the next atrial pacing pulse. In other examples, an initial atrial pacing escape interval may be set equal to the LRI upon sensing the first intrinsic atrial event upon RA pacemaker implantation.

If the atrial pacing escape interval expires at block 314 with no ventricular events sensed by FF event detector 224 of RA pacemaker 12 (or sensors 212) during the atrial pacing escape interval (negative result at block 306), and no intrinsic atrial events are sensed by NF event detector 222 during the atrial pacing escape interval (negative result at block 310), an atrial pacing pulse is delivered at block 316 at the established LRI. Upon delivering an atrial pacing pulse, the control module 206 of RA pacemaker 12 returns to block 302 to establish the atrial LRI by making any necessary adjustments based on a sensor-indicated rate and/or rate of FF ventricular events. The next atrial pacing escape interval is set to an AA interval equal to the LRI established at block 302.

If a ventricular event is sensed during the atrial pacing escape interval, however, as determined at block 306, the control module 206 of RA pacemaker 12 restarts the atrial pacing escape interval to a VA interval at block 308. The VA interval is set equal to the LRI established at block 302 less a target atrioventricular (AV) interval. The target AV interval may be retrieved from memory 210 of RA pacemaker 12. The target AV interval is the interval between an atrial pacing pulse and a subsequent ventricular event that is desired to achieve optimal timing between the atrial and ventricular contractions. A target AV interval may be determined for a given patient based on hemodynamic measurements or other optimization techniques or may be programmed to a nominal value. A programmed target AV interval stored in memory 210 of RA pacemaker 12 may be in the range of 100 to 300 ms, and more typically in the range of 150 to 250 ms. The target AV interval may be automatically adjusted with changes in the LRI established at block 302 to provide a shorter AV interval during episodes of higher pacing rates (shorter LRI) and a longer AV interval during relatively slower pacing rates (longer LRI).

A target AV interval may be stored in memory 210 for subtracting from the established LRI for setting a VA interval in response to an electrical FF ventricular event, and a different target AV interval may be stored in memory 210 for subtracting from the established LRI for setting a VA interval in response to a mechanical FF ventricular event. The S1 heart sound may be 10 to 50 ms later than an electrical R-wave for example. Accordingly, the target AV interval used in setting a VA interval in response to a mechanical FF ventricular event may be 10 to 50 ms shorter than a target AV interval used in setting a VA interval in response to an electrical FF ventricular event.

In some cases, the AV interval may be adjusted from a stored or programmed AV interval to coordinate the atrial pacing pulses and the ventricular pacing pulses. The RA pacemaker 12 may measure an actual AV delay time between an atrial pacing pulse and a subsequent FF ventricular event and adjust the AV interval used in setting the escape interval at block 308 to cause the actual AV delay time to match the targeted AV interval when AV conduction is intact.

If the atrial pacing escape interval (set to the VA interval at block 308) expires at block 314 without sensing an intrinsic atrial event by the NF event detector 222 at block 310, an atrial pacing pulse is delivered at block 316 by the RA pacemaker 12 at the expiration of the VA interval at block 314. By setting the atrial pacing escape interval to the LRI less the targeted AV interval, the next ventricular event, intrinsic or paced, will be preceded by an atrial pacing pulse delivered at approximately the target AV interval prior to the next ventricular event, assuming the ventricular rate is not changing significantly since a preceding cardiac cycle and no intervening atrial sense event occurs. In this way, the RA pacemaker 12 is configured to deliver ventricular-synchronized atrial pacing pulses that are coordinated with sensed FF ventricular events, electrical or mechanical.

In one example, a scheduled atrial pacing pulse is inhibited if an atrial event is sensed at block 310 during the atrial pacing escape interval, which may be either an AA interval set equal to the LRI at block 304 or a VA interval set equal to the LRI less the target AV interval at block 308. At block 312, the next atrial pacing pulse is scheduled to occur at the established LRI after the atrial sense event plus any unexpired time of the currently running escape interval.

The atrial pacing pulse scheduled to occur at the expiration of a previously started AA or VA interval is inhibited, and the next atrial pacing pulse may be scheduled by re-setting the atrial escape interval timer at block 312 upon sensing an atrial event by NF event detector 222 in some examples. The atrial pacing escape interval restarted at block 312 may be set to the currently established LRI plus all unexpired time remaining in the previously started atrial pacing escape interval at the time that the intrinsic atrial event was sensed during the escape interval. The unexpired time may be determined by the control module 206 and added to the LRI for resetting the escape interval timer, or the LRI may be added to any remaining time left on the escape interval timer at the time that the intrinsic atrial event is sensed.

Figure 5A:
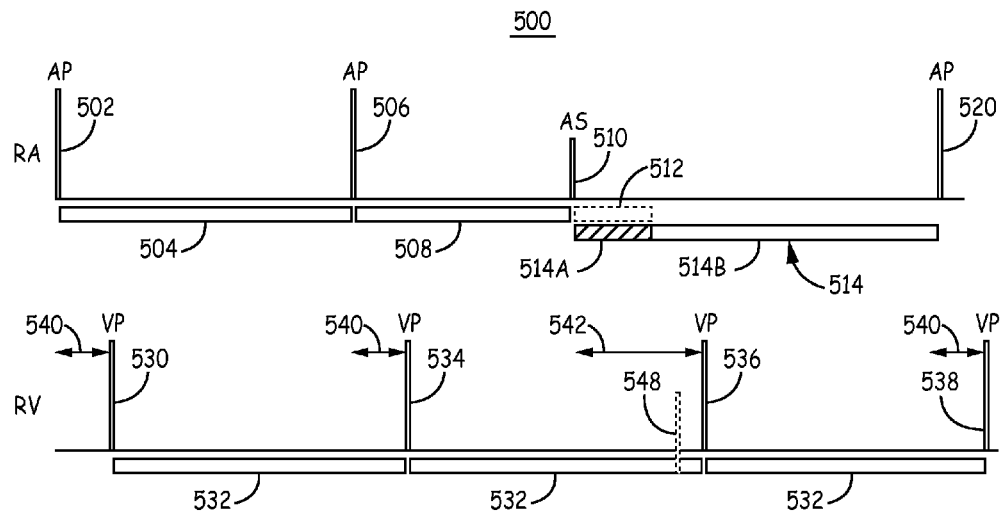
FIGS. 5A through 5C are timing diagrams illustrating methods for controlling atrial pacing pulse delivery by an atrial intracardiac pacemaker in the presence of atrial sense events.
Figure 5B:
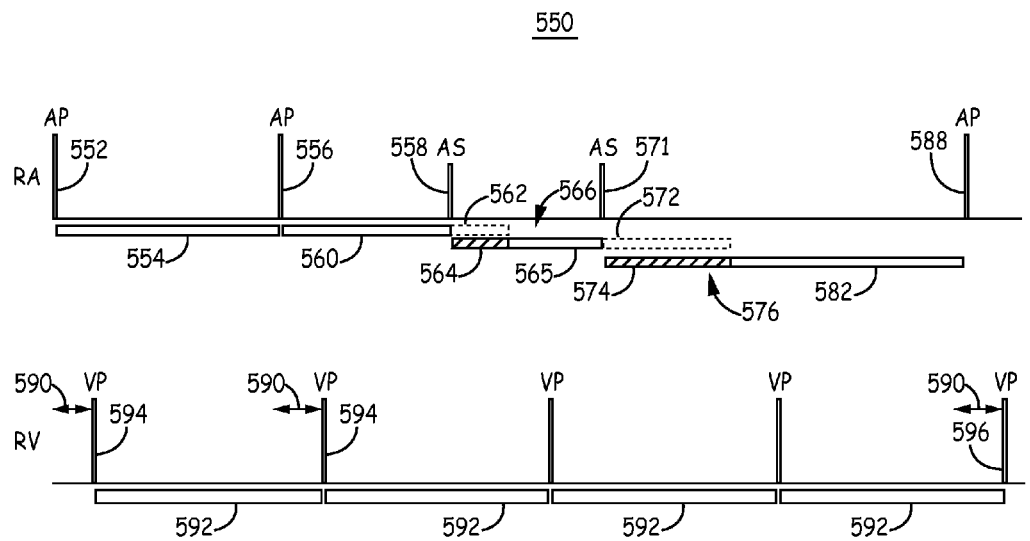

As such, if the escape interval timer was set to an AA interval in response to an atrial pacing pulse, the escape interval timer is reset in response to a NF atrial sense event signal received by the control module 206 to an atrial pacing escape interval that includes a sum of the established LRI and any time remaining in the unexpired AA interval upon receiving the NF atrial sense event signal from NF event detector 222. This situation is illustrated in FIGS. 5A and 5B. If the escape interval timer was set to a VA interval in response to a sensed FF ventricular event, the escape interval timer is reset in response to receiving a NF atrial sense event signal by the control module 206 to an atrial pacing escape interval that includes a sum of the established LRI and any time remaining in the unexpired VA interval upon receiving the NF atrial sense event signal from the NF event detector 222. Any time the atrial pacing escape interval expires at block 314, an atrial pacing pulse is delivered at block 316 and the process returns to block 302 to adjust the LRI if needed and set the next atrial pacing escape interval to an AA interval equal to the LRI at block 304.

If multiple NF atrial sense event signals are received without an intervening atrial pacing pulse or FF ventricular event, unexpired time on the atrial escape interval timer may accumulate over multiple intrinsic atrial cycles when the LRI is repeatedly added to any unexpired time remaining on the escape interval timer in response to each NF atrial sense event. This situation is described in conjunction with FIG. 5B.

Accumulation of unexpired time due to consecutively sensed atrial events may result in an inappropriately long atrial escape interval. Accordingly, at block 312, the control module 206 may set the atrial pacing escape interval to the established LRI plus unexpired time of the currently running escape interval within predefined limits or boundaries to avoid accumulation of unexpired escape intervals leading to an excessively long atrial pacing escape interval.

In one example, a maximum accumulated time limit that can be added to the established LRI in response to a NF atrial sense event signal may be defined. For example, a maximum accumulated unexpired time added to the established LRI may be equal to the established LRI so that the escape interval set at block 312 is never greater than twice the established LRI.

In another example, the atrial pacing escape interval set at block 312 may be set to an expected time of the next FF ventricular event of the next cardiac cycle less the target AV interval. If AV conduction is not intact, the ventricular rate may continue at a paced rate according to an established ventricular LRI. The NF atrial sensed event will not be conducted to the ventricles, but the next ventricular pacing pulse can be expected to occur at the established ventricular LRI. The expected time of the FF ventricular event of the next cardiac cycle may be based on previously measured intervals between FF ventricular events or the established atrial LRI assuming it approximately matches the ventricular LRI. Generally, the atrial pacing escape interval is set in response to a NF atrial sense event to provide an atrial pacing pulse at a VA interval after the next expected FF ventricular event of the current cardiac cycle or a target AV interval before the FF ventricular event of the next cardiac cycle.

In another example, at block 312 the control module 206 schedules the next atrial pacing pulse to occur at the atrial LRI plus any unexpired time of the current atrial pacing escape interval at the time the atrial event was sensed by allowing the unexpired atrial pacing escape interval to expire. At the expiration of the atrial pacing escape interval, the scheduled atrial pacing pulse is withheld, and the next atrial pacing escape interval is set equal to the atrial lower rate interval. This process of allowing the atrial pacing escape interval to expire, withholding a scheduled atrial pacing pulse and starting a next atrial pacing escape interval equal to the established LRI upon expiration of the atrial pacing escape interval allows atrial pacing pulses to be scheduled at regular intervals. Examples of atrial pacing escape intervals set in response to a NF atrial sensed event using this technique are described in FIG. 5C.

The VA interval started in response to a FF ventricular event contributes to the regulation of an actual AV delay within range of a target AV interval. The VA interval set as FF ventricular events are sensed also acts to prevent unexpired time from atrial pacing escape intervals from accumulating when consecutive NF atrial events are sensed without atrial pacing. Examples of setting a VA interval are described in conjunction with FIG. 6.

FIG. 5A is a timing diagram 500 illustrating one method for controlling atrial pacing pulse delivery by RA pacemaker 12. An initial atrial pacing pulse 502 causes the atrial pacing escape interval timer to be set to the atrial LRI 504 established by the RA pacemaker 12. The atrial LRI 504 may be set to the base pacing rate interval or set according to a sensor-indicated rate. When set according to a sensor-indicated rate, the atrial LRI 504 may be further adjusted to equalize the atrial pacing rate with a rate of FF ventricular events as described in conjunction with the flow chart of FIG. 7.

The next atrial pacing pulse 506 is delivered upon expiration of atrial LRI 504, causing the atrial pacing escape interval timer to be reset to the atrial LRI 508. An atrial sensed event 510 occurs during the atrial LRI 508, causing the atrial escape interval timer to be reset without delivering an atrial pacing pulse. The new atrial escape interval 514 set in response to the atrial sensed event 510 includes a portion 514A, equal to the unexpired time 512 of the previously started atrial LRI 508, plus a portion 514B equal to the established atrial LRI 504. The next atrial pacing pulse 520 is delivered upon expiration of this extended escape interval 514.

The extended escape interval 514 is set equal to the unexpired portion 512 of the previous atrial escape interval 508 plus the atrial LRI portion 514B in order to maintain a target AV interval 540 and to promote a regular ventricular rate (when AV conduction is intact). Atrial sense event 510 may be a premature atrial contraction, retrograde conduction of a ventricular event or other event which is not used by the RA pacemaker 12 to drive the atrial rate. Rather, it is used to schedule an atrial pacing pulse 520 at the target AV interval 540 ahead of an expected ventricular event 538 on the next cardiac cycle.

In the example shown, there is no intrinsic AV conduction such that RV pacemaker 14 is pacing the ventricle independently of atrial activity. RV pacemaker 14 may be delivering ventricular pacing pulses 530, 534, 536, and 538 at a stable ventricular LRI 532. The ventricular LRI 532 is set equal to a ventricular LRI established by the RV pacemaker 14, which may be a programmed base rate interval or shortened from the base rate interval to a SIR interval. The ventricular pacing pulses 530 and 534 arrive at a target AV interval 540 following the atrial pacing pulses 502 and 506.

If the RV pacemaker pacing rate is constant at the ventricular LRI 532, ventricular pacing pulse 536 arrives after the atrial sensed event 510 at an actual AV delay time interval 542 that is much longer than the target AV interval 540. By setting the extended escape interval 514 following the atrial sensed event 510, however, the next atrial pacing pulse 520 is delivered at the target AV interval 540 prior to the ventricular pacing pulse 538 in the next cardiac cycle.

In this way, even if sensing of the FF ventricular events (i.e., pacing pulses 530, 534, 536 and 538, evoked R-wave associated therewith, or associated mechanical events) intermittently disappears, the RA pacemaker 12 is able to maintain atrial pacing coordinated with the regular ventricular rate determined before sensing of FF ventricular events was lost by setting the extended escape interval 514 in response to atrial sense event 510. Atrial pacing pulse 520 is delivered at approximately the target AV interval 540 prior to the expected FF ventricular event corresponding to ventricular pacing pulse 540 on the next cardiac cycle after the NF atrial sense event 510.

If AV conduction returns, ventricular depolarizations conducted from the atria may cause ventricular pacing to be inhibited. If the early atrial sense event 510 is conducted to the ventricles, a ventricular event 548 may occur after an intrinsic AV conduction time that does not match the target AV interval. If this occurs, the ventricular rate increases for one cardiac cycle, and the ventricular pacing pulse 536 is inhibited. However, a regular ventricular rate will be resumed on the next cardiac cycle by applying the extended atrial escape interval 514 that includes an unexpired portion 512 of the previous atrial escape interval 508.

If the intrinsic atrial rate is actually increasing, e.g., during sinus tachycardia, consecutive atrial sensed events will inhibit the atrial pacing pulses. If AV conduction is intact, the ventricular rate naturally follows the atrial rate. If AV conduction is blocked, the RV pacemaker adjusts the ventricular LRI according to a sensor-indicated rate. The RA pacemaker 12 will track the rate of the FF ventricular events and if the atrial sinus rate is lagging or leading the FF ventricular event rate, the atrial LRI is adjusted to match the FF ventricular event intervals according to techniques described below in conjunction with FIG. 7.

FIG. 5B is a timing diagram 550 illustrating a method for setting atrial pacing escape intervals in response to atrial sense events in the absence of FF ventricular event sensing according to another example. Atrial pacing pulses 552, 556 are delivered at an established atrial LRI 554. Ventricular pacing pulses 594 are delivered at an established ventricular LRI 592. The atrial pacing pulses 552 and 556 arrive at the target AV interval 590 prior to the ventricular pacing pulses 594. Atrial sense event 558 occurs during the atrial LRI 560, which may cause the atrial pacing escape interval timer to be reset to an atrial pacing escape interval 566 that includes a first portion 564 equal to the unexpired portion 562 of atrial LRI 560 plus a second portion 565 equal to the atrial LRI 554.

Another atrial sense event 571 is sensed during the second portion 565 of atrial pacing escape interval 566. An unexpired portion 572 of escape interval 566 remains at the time of atrial sense event 571. A new atrial pacing escape interval 576 is started including a portion 574 equal to the unexpired time 572 of the previous escape interval 566 added to a portion 582 equal to the atrial LRI 554. The total atrial pacing escape interval 576 includes unexpired time 572 that is an accumulation of unexpired time of the atrial LRI during the preceding two escape intervals 560 and 566 during which atrial sense events 558 and 571 occur.

Upon expiration of atrial escape interval 576, an atrial pacing pulse 588 is delivered. Atrial pacing pulse 588 occurs at the target AV interval 590 ahead of the ventricular pacing pulse 596 in this example because the unexpired portions 562 and 572 of the previous two pacing escape intervals 560 and 566 have been tracked by incorporating these unexpired LRI portions 562 and 572 in the atrial pacing escape interval 576. If the ventricular rate has not changed, which in this example has been controlled by a constant ventricular LRI 592, the atrial pacing pulse 588 arrives at the target AV interval 590 ahead of ventricular pacing pulse 596 achieving atrial-ventricular synchrony despite withholding atrial pacing pulses for two atrial cycles and without sensing FF ventricular events.

As observed in FIG. 5B, the unexpired times 562, 572 of the atrial pacing escape intervals 560, 566 may accumulate in the next escape interval 576 when consecutive atrial sense events occur at intervals shorter than the atrial LRI without any ventricular sense events. If this process of adding unexpired time to the LRI in response to successive atrial sense events continues over an extended period of time, however, the accumulated unexpired time of previous atrial pacing escape intervals added to the atrial LRI 554 may lead to an excessively long atrial pacing escape interval. If no intrinsic atrial events occur during the excessively long atrial pacing escape interval, a period of atrial asystole could result. In order to avoid an excessively long atrial pacing escape interval, the extended escape intervals 566, 576 may be limited to a maximum of twice the atrial LRI 554 in one example.

In other examples, therefore, control module 206 may extrapolate the expected time of a future ventricular event based on previously determined sensed FF ventricular event intervals and schedule an atrial pacing pulse according to an expected ventricular event time. During an extended period of atrial sensing in the absence of intrinsic AV conduction, however, the ventricular rate could change such that when an atrial pacing pulse is ultimately delivered, it may not arrive within an acceptable range of the target AV interval 590 of a ventricular pacing pulse.

Figure 5C:
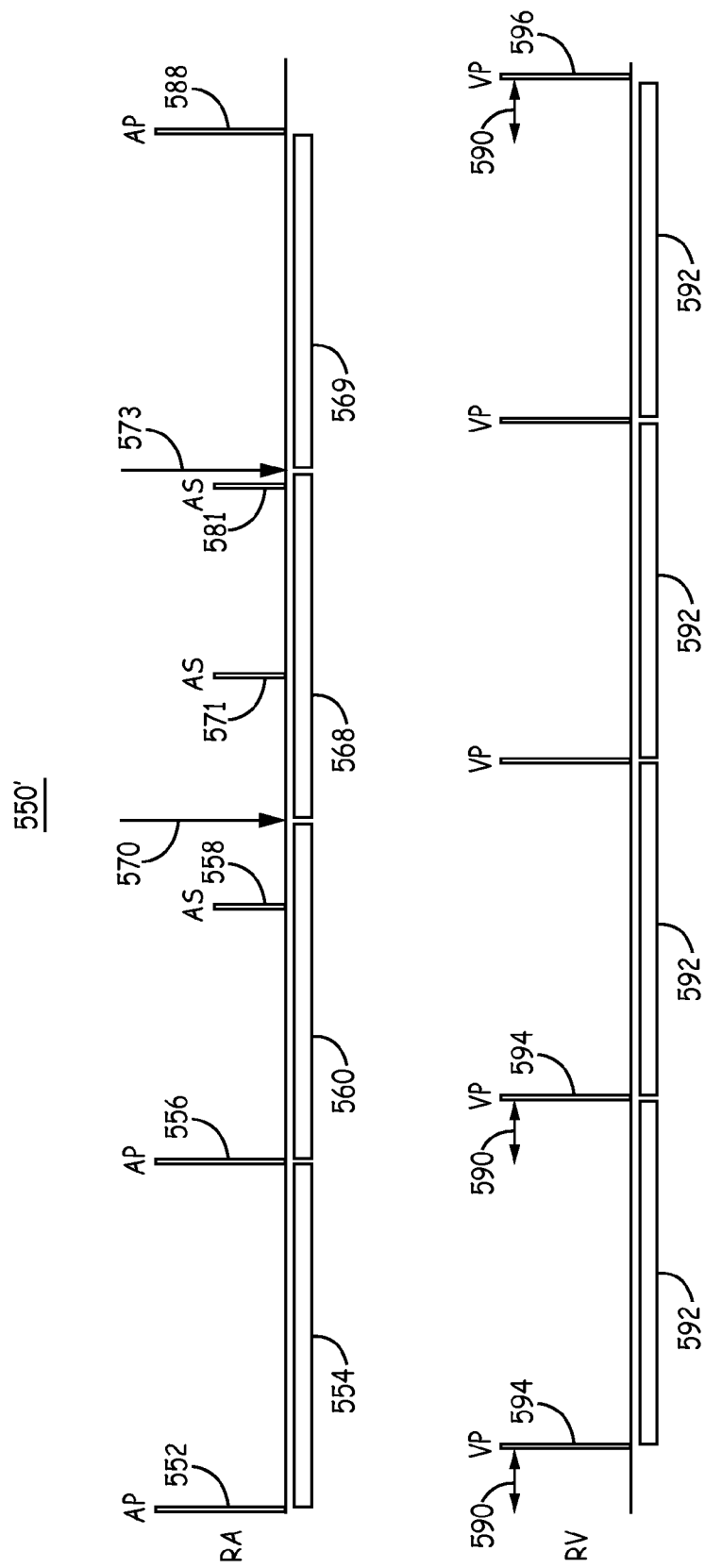

FIG. 5C is a timing diagram 550' illustrating an alternative method for setting atrial pacing escape intervals in the presence of atrial sense events and absence of FF ventricular event sensing. Timing diagram 550' includes the identically-numbered atrial pacing pulses 552 and 556 delivered at atrial LRI 554, ventricular pacing pulses 594 delivered at a ventricular LRI 592, and atrial sense events 558 and 571 as shown in FIG. 5B. A third atrial sense event 581 is shown to occur consecutively after atrial sense events 558 and 571. In this example, the control module 206 does not restart the atrial pacing escape interval timer in response to atrial sense events 558, 571, and 581.

The atrial pacing escape interval 560 started upon delivery of atrial pacing pulse 556 is allowed to expire even though an atrial sense event 558 occurs during the escape interval 560. The control module 206, however, inhibits the atrial pacing pulse scheduled at the expiration 570 of atrial pacing escape interval 560 in response to atrial sense event 558. The control module 206 restarts the pacing escape interval timer at the expiration 570 of escape interval 560. The pacing escape interval timer is set to a new atrial pacing escape interval 568 equal to the atrial LRI 554.

In response to atrial sense event 571, which occurs during atrial pacing escape interval 568, the pacing pulse scheduled at the expiration 573 of escape interval 568 is withheld. A new pacing escape interval 569 equal to the atrial LRI 554 is started at expiration 573. A second atrial sense event 581 occurs during atrial pacing escape interval 568. The second atrial sense event 581 is ignored for purposes of controlling the pacing escape interval timer. If more than one atrial sense event occurs during a single atrial pacing escape interval 568, the additional sense event signals may be ignored; no additional response to the atrial sense events beyond the first atrial sense event is taken. The pacing escape interval 568 continues running, and the scheduled pacing pulse at its expiration 573 remains inhibited.

At the expiration of pacing escape interval 568, no pacing pulse is delivered, but a new pacing escape interval 569 equal to the atrial LRI 554 is started. This escape interval 569 expires resulting in delivery of atrial pacing pulse 588 by pulse generator 202. In this way, atrial sense events 558, 571 and 581 do not disrupt the regularity of the atrial pacing escape intervals 560, 568 and 569 each set to the atrial LRI but do inhibit atrial pacing pulses to avoid a sequence of combined intrinsic and paced intervals that lead to an overall fast atrial rate. When an atrial escape interval 569 eventually expires, the atrial pacing pulse 568 is delivered at the target AV interval 590 ahead of ventricular pacing pulse 596 if the ventricular rate has not changed, which in this example is controlled by a constant ventricular LRI 592.

Figure 6:
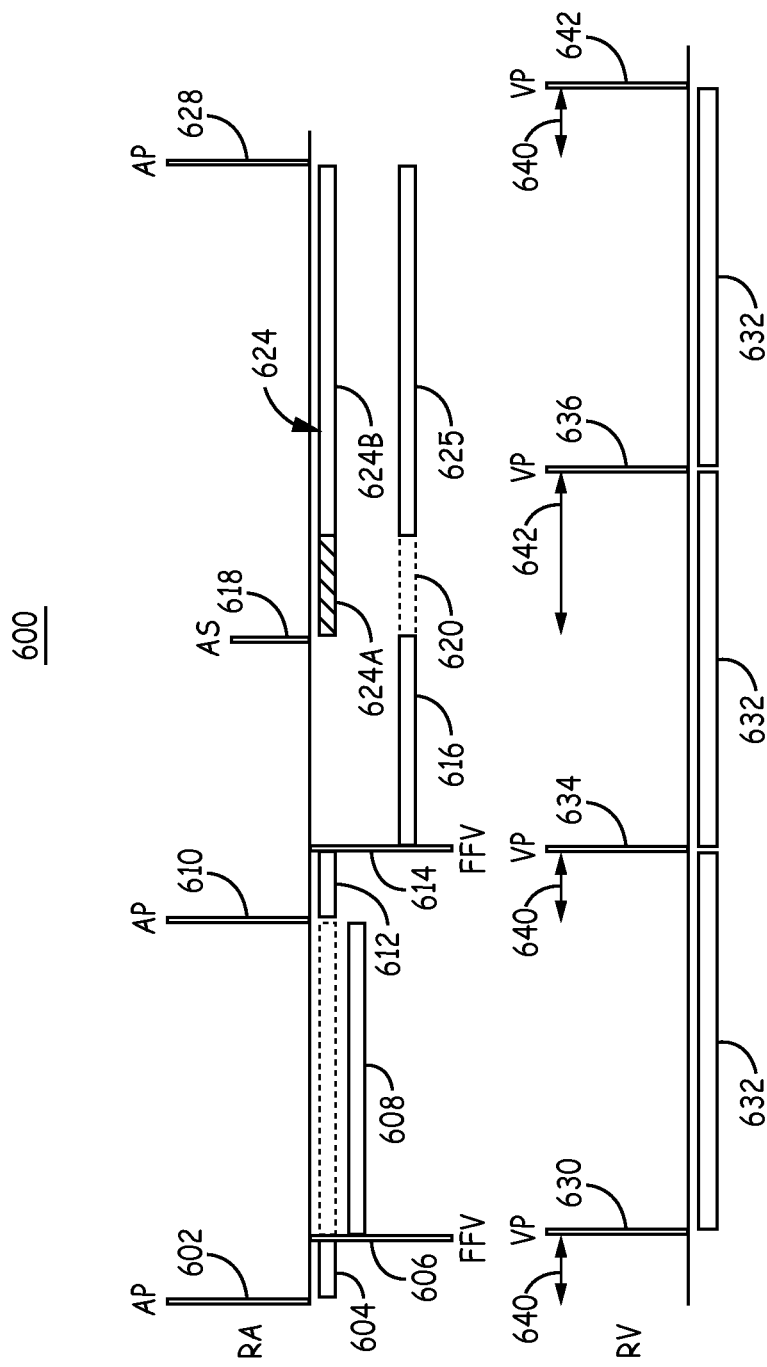
FIG. 6 is a timing diagram illustrating methods for controlling atrial pacing pulse delivery by an atrial intracardiac pacemaker in the presence of ventricular sense events.

FIG. 6 is a timing diagram 600 illustrating a method for controlling atrial pacing pulse delivery by RA pacemaker 12 according to another example. In the example of FIG. 6, the RA pacemaker 12 is sensing FF ventricular events 606 and 614. Atrial pacing pulse 602 causes the control module 206 of RA pacemaker 12 to set the atrial escape interval timer to start an atrial LRI 604 equal to the established LRI. During the atrial LRI 604, however, a FF ventricular event 606 is sensed by RA pacemaker 12, causing the atrial escape interval timer to be reset from the started atrial LRI 604 to a VA escape interval 608. VA escape interval is set equal to the established atrial LRI 604 less the target AV interval 640. The target AV interval 640 subtracted from the LRI to set the VA escape interval 608 may take into account delays between an actual ventricular event and the time that the FF ventricular event 606 is sensed by the RA pacemaker 12.

Upon expiration of the VA escape interval 608, atrial pacing pulse 610 is delivered. An atrial LRI 612 is started in response to the atrial pacing pulse 610. Another sensed FF ventricular event 614 causes the escape interval timer to be reset to a VA escape interval 616 equal to the established atrial LRI less the target AV interval 640. Both atrial pacing pulses 602 and 610 are delivered at a target AV interval 640 prior to the subsequent ventricular pacing pulses 630 and 634, respectively.

Prior to expiration of VA escape interval 616, an intrinsic atrial event 618 is sensed by RA pacemaker 12. The atrial sensed event 618 causes the atrial escape interval timer to be reset to an extended escape interval 624 that includes first portion 624A equal to the unexpired portion 620 of the VA escape interval 616 at the time the atrial event 618 was sensed and a second portion 624B equal to the established atrial LRI, which may be based on an atrial sensor-indicated rate and adjusted from the atrial sensor-indicated rate to match the ventricular rate as described below. By extending the escape interval 624 by the unexpired portion 620 of the previous VA escape interval 616, the next atrial pacing pulse 628 occurs at the target AV interval 640 prior to the next ventricular pacing pulse 642, which is delivered at the ventricular LRI 632.

In this example, the ventricular pacing pulse 636 is not sensed as a FF ventricular event by RA pacemaker 12. It occurs at an actual AV delay time interval 642 following the atrial sensed event 618 that is longer than the target AV interval 640. By setting an extended escape interval 624, however, the target AV interval 640 is re-established on the next cardiac cycle. If the ventricular pacing pulse 636 is sensed by the RA pacemaker 12 as a FF ventricular event, the escape interval 624 is restarted as a VA interval equal to the atrial LRI less the target AV interval to also arrive at an atrial pacing pulse 628 delivered at the target AV interval 640 prior to ventricular pacing pulse 642.

In an alternative example, if an atrial sense event 618 occurs during the VA interval 616, the VA interval 616 is allowed to expire, and a new atrial pacing escape interval 625 set equal to the established atrial LRI is started upon the expiration of VA interval 616. The atrial pacing pulse that was scheduled to occur at the expiration of the VA escape interval 616 is withheld. The next atrial pacing pulse 628 is scheduled to occur at the expiration of the atrial LRI (escape interval 625) plus any unexpired time 620 of the currently running VA escape interval 616 at the time of the atrial sensed event 618 by allowing VA escape interval 616 to expire, withholding the scheduled pacing pulse, and starting an AA escape interval 625 set to the established LRI.

The methods depicted by the timing diagrams 500, 550, 550' and 600 of FIGS. 5A, 5B, 5C and FIG. 6 promote regular atrial and ventricular rates synchronized at a target AV interval even when an intrinsic atrial event is occasionally sensed during an atrial escape interval set to an AA or VA interval.

Some techniques disclosed in conjunction with the flow charts and timing diagrams presented herein for controlling an atrial pacing escape interval timer of an atrial intracardiac pacemaker may be used for controlling a ventricular pacing escape interval timer of a ventricular intracardiac pacemaker. For instance, a ventricular pacemaker sensing module may be configured to sense near field events occurring in the ventricle and far-field events occurring in the atria. The ventricular pacemaker may be configured to respond to sensed events by withholding a scheduled pacing pulse in the ventricle and controlling a ventricular pacing escape interval timer based on the timing of near-field and far-field events sensed in the ventricle.

Figure 7:
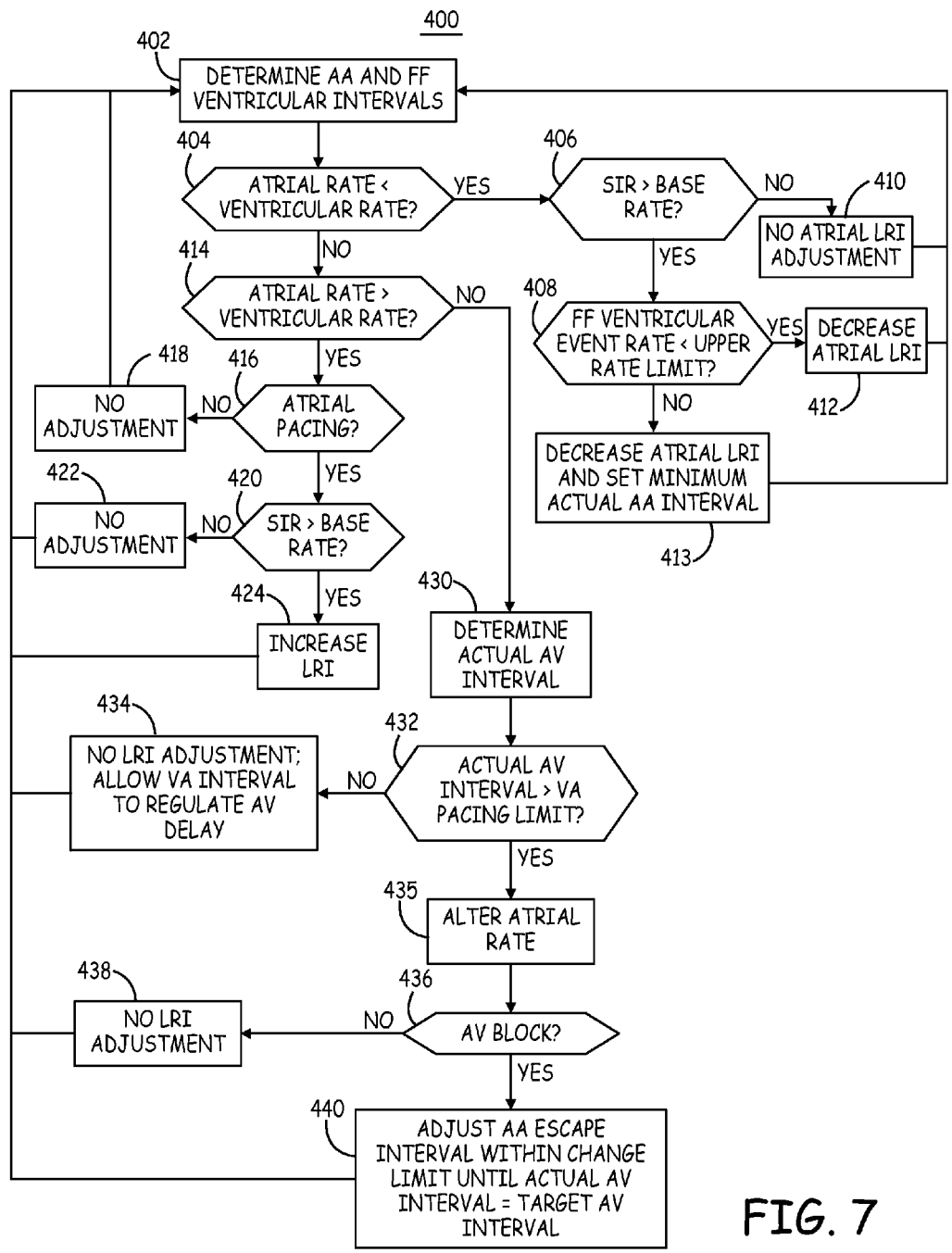
FIG. 7 is a flow chart of a method for controlling an atrial intracardiac pacemaker to provide coordinated dual chamber pacing.

FIG. 7 is a flow chart 400 of a method for controlling RA pacemaker 12 to provide atrial pacing coordinated with ventricular events. RA pacemaker 12 may be configured to deliver atrial pacing pulses, sense NF intrinsic atrial events and FF ventricular events (dual chamber sensing) and inhibit atrial pacing pulses in response to sensing NF intrinsic atrial events and schedule atrial pacing pulses in response to sensing FF ventricular events. By providing dual chamber sensing in the RA pacemaker 12, the RA pacemaker 12 can track ventricular events to provide coordinated dual chamber pacing in an IMD system that includes separate RA pacemaker 12 and RV pacemaker 14 without requiring wireless telemetry communication between the telemetry modules 208 of the respective RA and RV pacemakers 12 and 14 and without requiring FF sensing of atrial events by the RV pacemaker 14. The timing of the atrial pacing pulses, as described above, may be controlled by setting an escape interval timer to a VA interval when an electrical FF ventricular event is sensed by FF event detector 224, which may be a ventricular pacing pulse or an R-wave, or when a mechanical FF ventricular event is sensed by sensors 212. The FF sensed event may be a physiological event, either intrinsic or evoked, or a therapeutic pacing pulse delivered to pace the ventricle that is not a communication signal or other non-therapeutic signal transmitted from the RV pacemaker 14 to the RA pacemaker 12.

The RV pacemaker 14 may be programmed for delivering ventricular pacing pulses, sensing ventricular intrinsic events, and inhibiting ventricular pacing pulses in response to sensing a ventricular intrinsic event. When AV conduction is intact, RA pacemaker 12 will drive the atrial rate and the ventricular rate will follow through the normal conduction system of the heart. When AV conduction is lost, RV pacemaker 14 will drive the ventricular rate, which may be a programmed lower base rate when rate responsive pacing is disabled or a sensor-indicated rate when rate responsive pacing is enabled. The RV pacemaker 14 will operate independent of the RA pacemaker 12 when intrinsic AV conduction is blocked. The RA pacemaker 12, however, will track the rate of FF ventricular events when the rate of the FF ventricular events is below a maximum tracking rate.

In order to maintain coordinated atrial and ventricular rates if AV conduction is lost, the control module 206 of RA pacemaker 12 is configured to determine and compare a rate of FF ventricular events and a rate of atrial events (paced and/or sensed) by determining AA and FF ventricular intervals (i.e., VV intervals) at block 402. If the atrial rate is less than (or greater than) the ventricular rate, AV conduction may be lost and the RV pacemaker 14 may be pacing the ventricle at a higher (or lower) rate than the intrinsic or paced atrial rate.

AA and VV intervals may be determined and compared beat-by-beat, by determining and comparing a median or mean of N consecutive intervals, by determining a running average of N consecutive intervals or other methods. In some examples, the rates may be considered equal if a determined AA interval measurement and a determined VV interval measurement are within a threshold difference of each other, e.g., within 10 ms of each other. However, a small, sustained difference between AA and VV intervals can accumulate over time causing a shift of the atrial events relative to the ventricular events such that a target AV interval is lost. One or more atrial pacing pulses at a modified AA interval(s) may be delivered to bring the actual AV delay back within an acceptable range of a target AV interval, e.g., according to the flow chart of FIG. 7.

If the atrial rate is less than the ventricular rate, as determined at block 404, the control module 206 of RA pacemaker 12 determines if the atrial rate response function is active at decision block 406 as evidenced by an atrial sensor-indicated rate that is greater than the programmed base rate. If the atrial rate response function is active, indicating that a pacing rate greater than the programmed base pacing rate is warranted, the RV pacemaker rate response function is likely to be active as well. The RV pacemaker rate response function, however, may be producing a sensor-indicated rate that is greater than the sensor-indicated rate determined by the RA pacemaker 12. It is desirable to control the RA pacemaker 12 to track the higher ventricular rate to maintain coordinated atrial and ventricular activity as long as the higher ventricular rate is duly warranted based on patient metabolic demand and not due to ventricular tachyarrhythmia.

Accordingly, if the atrial rate response is inactive as indicated by a SIR that is not greater than the programmed base pacing rate (at block 406), the faster FF ventricular event rate may be due to ventricular tachyarrhythmia. No adjustment to the atrial LRI is made at block 410. The RA pacemaker 12 will not track the faster ventricular rate when the RA pacemaker control module 206 determines that an increased pacing rate is unwarranted based on the atrial rate response function being inactive, i.e., not producing a sensor-indicated rate greater than the base pacing rate.

If the atrial rate response function is actively producing a sensor-indicated rate greater than the programmed atrial base pacing rate as determined at block 406, the RA pacemaker control module 206 determines if the rate of FF ventricular events sensed by the RA pacemaker 12 is less than a ventricular tracking upper rate limit (block 408). A ventricular tracking upper rate limit may be programmed in RA pacemaker memory 210. In one example, if the ventricular rate is greater than the tracking upper rate limit, there is no adjustment to the atrial LRI being used by the RA pacemaker 12 (block 410). The FF ventricular event rate that is determined to be greater than the atrial rate at block 404 may be due to ventricular tachyarrhythmia, and therefore atrial tracking of the higher ventricular rate may be undesirable.

The RA pacemaker 12 may be configured to control the atrial pacing rate to track a rate of FF ventricular events up to upper rate limit by shortening the atrial LRI at block 412. The upper rate limit may be as high as 120 to 140 bpm, for example. In practice, the upper rate limit may less than 120 bpm, e.g., 100 bpm, since FF ventricular event sensing may be less reliable at higher heart rates and because AV synchrony is typically more important at rest. If the rate of FF ventricular events exceeds the upper rate limit, the RA pacemaker 12 continues to use the atrial LRI established according to the sensor indicated rate determined by the control module 206 of RA pacemaker 12 without adjustment of the atrial LRI in response to the higher FF ventricular event rate (a direct path from block 408 to block 410 not shown in FIG. 7).

Alternatively, if the FF ventricular events exceed an upper rate limit, at block 408, the atrial LRI may be decreased at block 413 to equalize the atrial and ventricular rates, but a minimum AA interval limit may be set. Atrial pacing pulses may be delivered at the expiration of a VA interval set based on the decreased atrial LRI when a FF ventricular event is sensed as long as the resulting actual AA interval is greater than a minimum AA interval limit. In this way, a maximum atrial rate is controlled by inhibiting atrial pacing pulses during a fast ventricular rate only when an atrial pacing pulse would result in an actual AA interval less than a minimum limit. To illustrate, atrial pacing pulses may be delivered at the expiration of every other VA interval when atrial pacing synchronized to every FF ventricular event results in an actual AA interval that is less than a minimum AA interval limit. In this way, atrial pacing pulses that are delivered are synchronized to ventricular events during a faster ventricular rate, but an unacceptable, pacing-induced fast atrial rate is avoided.

If the FF ventricular event rate is less than the upper rate limit at block 408, the FF ventricular event rate may be a valid sensor-indicated rate produced by the control module 206 of the RV pacemaker 14. The ventricular sensor-indicated rate produced by the RV pacemaker 14 may be higher than the sensor-indicated rate produced by the RA pacemaker 12, causing the atrial rate to be less than the ventricular rate. If the sensor-indicated rate produced by the RV pacemaker 14 is slightly greater than the sensor-indicated rate produced by the RA pacemaker 12, this discrepancy may cause the atrial pacing rate to lag the ventricular paced rate, resulting in uncoordinated atrial and ventricular activity. The increased FF ventricular event rate, however, is determined to be warranted due to an active rate response of the RA pacemaker 12 producing a SIR greater than the base rate and not likely due to ventricular tachyarrhythmia.

In this situation, atrial tracking of the ventricular rate is desirable. At block 412, the control module 206 of RA pacemaker 12 decreases (shortens) the currently established atrial LRI. The atrial LRI may be decreased in a step-wise manner according to the step resolution of the atrial pacing escape interval timer of the RA pacemaker 12. Alternatively, a difference interval that is the difference between one or more FF ventricular event intervals (or an averaged FF ventricular event interval) and one or more AA intervals (or an averaged AA interval) may be determined at block 412. The atrial LRI may be decreased by the determined difference interval so that the FF ventricular event intervals and the AA intervals are approximately equal, e.g., within 10 ms of each other.

The process then returns to block 402 to determine the AA and FF ventricular event intervals again. If the atrial rate is still less than the ventricular rate after adjusting the atrial LRI, the atrial LRI may continue to be adjusted at block 412, as long as the FF ventricular event rate remains below a ventricular tracking upper rate limit, until the FF ventricular event rate is no longer greater than the atrial rate, as determined by a negative result at decision block 404.

Figure 8:
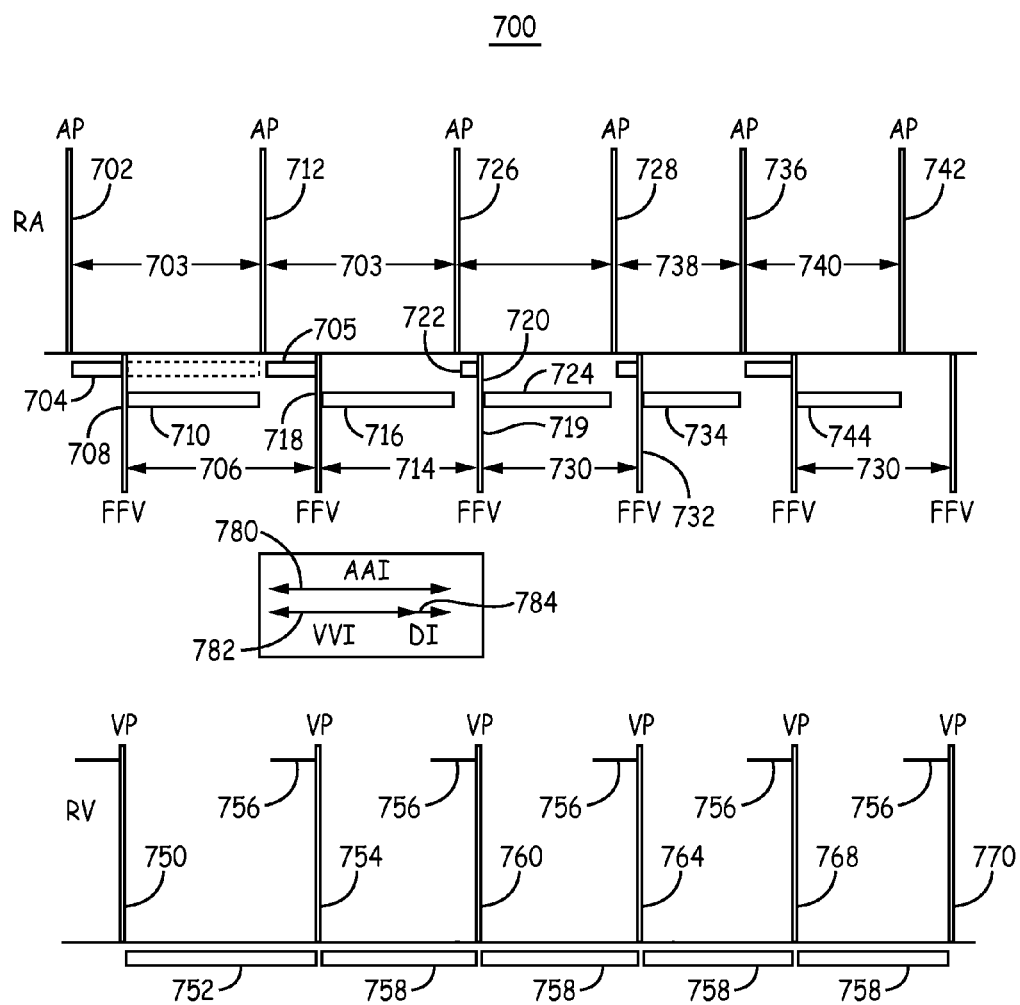
FIGS. 8 through 11 are timing diagrams illustrating operations shown in the flow chart of FIG. 7 for controlling atrial pacing pulse delivery by an atrial intracardiac pacemaker for delivering coordinated atrial and ventricular pacing using separate intracardiac pacemakers.

FIG. 8 is a timing diagram 700 of pacing pulses delivered by RA pacemaker 12 and RV pacemaker 14 illustrating the operation of RA pacemaker 12 for controlling atrial pacing pulse delivery when the sensed FF ventricular event rate is faster than the atrial rate ("yes" branch of block 404 in flow chart of FIG. 7). Atrial pacing pulses 702 and 712 are delivered at an established atrial LRI 703. Atrial LRI 703 may be based on a sensor-indicated rate by the control module 206 of RA pacemaker 12.

Ventricular pacing pulses 750 and 754 are delivered at the ventricular LRI 752 established by RV pacemaker 14. The FF ventricular event rate interval 706 may be stable prior to atrial pacing pulse 702 and up to atrial pacing pulse 712 due to a stable ventricular LRI 752. The atrial pacing pulses 702, 712 and 726 start the atrial pacing escape interval timer at the AA intervals 704, 705, and 722 set equal to the established atrial LRI 703. The atrial pacing escape interval timer is restarted during each of these AA intervals 704, 705 and 722 in response to sensing the respective FF ventricular events 708, 718, and 719. Upon each FF ventricular event 708, 718, and 719, the atrial pacing escape interval is set to a VA escape interval 710, 716, and 724, respectively, which is equal to the atrial LRI 703 less the target AV interval 756. Atrial pacing pulses 726 and 728 are delivered at the expiration of the VA escape intervals 716 and 724 set based on the atrial LRI 703.

As described below, a change in the ventricular rate is detected by RA pacemaker 12 between atrial pacing pulse 726 and atrial pacing pulse 728. The next VA escape interval 734 is set based on an adjusted atrial LRI and is therefore shorter than the preceding VA escape intervals 710, 716 and 724.

The ventricular LRI 752 is adjusted to a shorter LRI 758 following ventricular pacing pulse 754, e.g., in response to a sensor indicated pacing rate determined by the control module 206 of the RV pacemaker 14. Ventricular pacing pulse 760 is delivered upon expiration of a ventricular pacing escape interval set equal to the adjusted ventricular LRI 758 and is sensed as a FF ventricular event 720. FF ventricular event 720 occurs early in the target AV interval 756 due to the shortened ventricular LRI 758. Likewise, the next ventricular pacing pulse 764 occurs early in the target AV interval 756 due to the discrepancy between the previously established atrial LRI 703 used to set the VA escape interval 724 and the newly shortened ventricular LRI 758.

As described in conjunction with the flow chart 400 of FIG. 7, RA pacemaker 12 monitors the FF ventricular event rate based on determining the FF ventricular event intervals 706, 714, 730. While only two shortened FF ventricular event intervals 714 and 730 are shown, it is understood that the RA pacemaker 12 may monitor more than two FF ventricular event intervals before adjusting the atrial LRI to match the FF ventricular event rate. In this example, as few as two FF ventricular event intervals 714 and 730 are used to detect an atrial rate that is slower than the FF ventricular event rate. The control module 206 of the RA pacemaker 12 determines an AA interval (AAI) 780 (shown in the center, inset box), which is equal to the LRI 703 during ongoing atrial pacing in this example. AAI 780 is compared to a VV interval (VI) 782 that is determined from FF ventricular event intervals 714 and 730. An atrial rate slower than the ventricular rate is detected in response to the comparison of the AA interval 780 and the VV interval 782. A difference interval 784 may be determined as the difference between the AA interval 780 and the VV interval 782. The atrial LRI 703 is decreased by the difference interval 784 to an adjusted atrial LRI that matches the determined FF ventricular event interval 782 (and newly established ventricular LRI 758).

This shorter adjusted atrial LRI is used to set the next atrial escape interval 734 in response to the sensed FF ventricular event 732. This atrial escape interval 734 is set as a VA interval that is equal to the adjusted atrial LRI less the target AV interval 756. The next atrial pacing pulse 736 is delivered at a shortened AA interval 738 due to the relatively early sensed FF ventricular event 732 starting the VA escape interval 734, now set using the shortened atrial LRI. This results in atrial pacing pulse 736 being delivered at the target AV interval 756 prior to the next ventricular pacing pulse 768. On the next cardiac cycle, the atrial rate indicated by AA interval 740 (equal to the adjusted atrial LRI) matches the FF ventricular event interval 730 and corresponding ventricular LRI 758. The atrial pacing pulse 742 delivered at the expiration of the VA escape interval 744 set based on the adjusted atrial LRI arrives prior to the ventricular pacing pulse 770 at the target AV interval 756. In this way, the RA pacemaker 12 controls atrial pacing pulse delivery to match a ventricular rate determined from sensed FF ventricular events and restores the target AV interval 756 prior to ventricular pacing pulses when the ventricular rate accelerates ahead of the atrial rate. As described in conjunction with the flow chart 400 of FIG. 7, the RA pacemaker operation for shortening the established atrial LRI to match the atrial rate to a faster FF ventricular event rate is performed when the atrial rate response function is active and the FF ventricular event rate is below an upper rate limit.

Returning to the flow chart 400 of FIG. 7, the operation of the RA pacemaker 12 during the opposite situation of the atrial rate being faster than a sensed FF ventricular event rate (as determined at decision block 414) is now described. In response to an affirmative result at block 414, the control module 206 of RA pacemaker 12 determines if the AA intervals used to determine the atrial rate include atrial paced intervals. If at least one AA interval is a paced interval as determined at block 416, the process may advance to block 420. In other examples, if at least a majority of the AA intervals used for the rate comparison that resulted in the atrial rate being faster than the FF ventricular event rate are paced intervals, the process advances to block 420. In still another example, all of the AA intervals used in the comparison at block 414 that resulted in a determination of the atrial rate being greater than the FF ventricular event rate may be required to be paced intervals in order to advance to block 420.

If the AA intervals used to determine the atrial rate do include a required number of atrial paced intervals (affirmative result at block 416), an adjustment to the atrial LRI may be used to slow down the atrial rate that is currently running faster than the FF ventricular event rate. At block 420, the control module 206 of RA pacemaker 12 determines if the atrial rate response function is active, i.e., producing a sensor-indicated rate that is greater than the programmed base rate. If the atrial rate response function is not active, i.e., if a sensor-indicated rate is not being produced by the control module 206 for driving the atrial pacing rate higher than the programmed base rate, then no adjustment is made to the atrial pacing control parameters at block 422. The atrial pacing continues at the currently established LRI, which is the base pacing rate when atrial rate response is inactive. The atrial pacing rate is not slowed below a base pacing rate if the FF ventricular event rate is slower than the atrial pacing rate. The FF ventricular event rate determined to be slower than the atrial rate by RA pacemaker 12 may be due to undersensing of FF ventricular events by the RA pacemaker sensing module 204. In some cases, a discrepancy may exist between the lower base pacing rates programmed in the RV pacemaker 14 and in the RA pacemaker 12, or other therapy control parameters may exist causing the slower FF ventricular event rate.

If the atrial rate is being driven by a sensor-indicated rate that is above the programmed base pacing rate ("yes" branch of block 420), the atrial LRI is lengthened at block 424 to slow the paced atrial rate to bring it within an acceptable range of or equal to the FF ventricular event rate. The atrial LRI may be increased gradually in a step-wise manner at block 424 until the atrial rate is no longer greater than the ventricular rate (as determined by returning to block 402). Alternatively, a difference interval between AA intervals and FF ventricular event intervals may be determined at block 424. The atrial LRI may be increased (in one or more increments) by the determined difference interval at block 424 to approximately equalize the atrial and FF ventricular event rates.

If the AA intervals do not include a required number of paced intervals at block 416, the atrial rate is an intrinsic atrial rate that is faster than the rate of sensed FF ventricular events. Atrial pacing cannot be used to slow down the atrial rate; therefore no adjustment to an atrial LRI is made is made at block 418. Atrial pacing is inhibited by the sensed intrinsic atrial activity occurring at a rate faster than the currently established atrial LRI. Undersensing of FF ventricular events by FF event detector 224 may cause the RA pacemaker control module 206 to detect an atrial rate faster than a FF ventricular event rate or the faster atrial rate may be caused by an atrial tachyarrhythmia.

Figure 9:
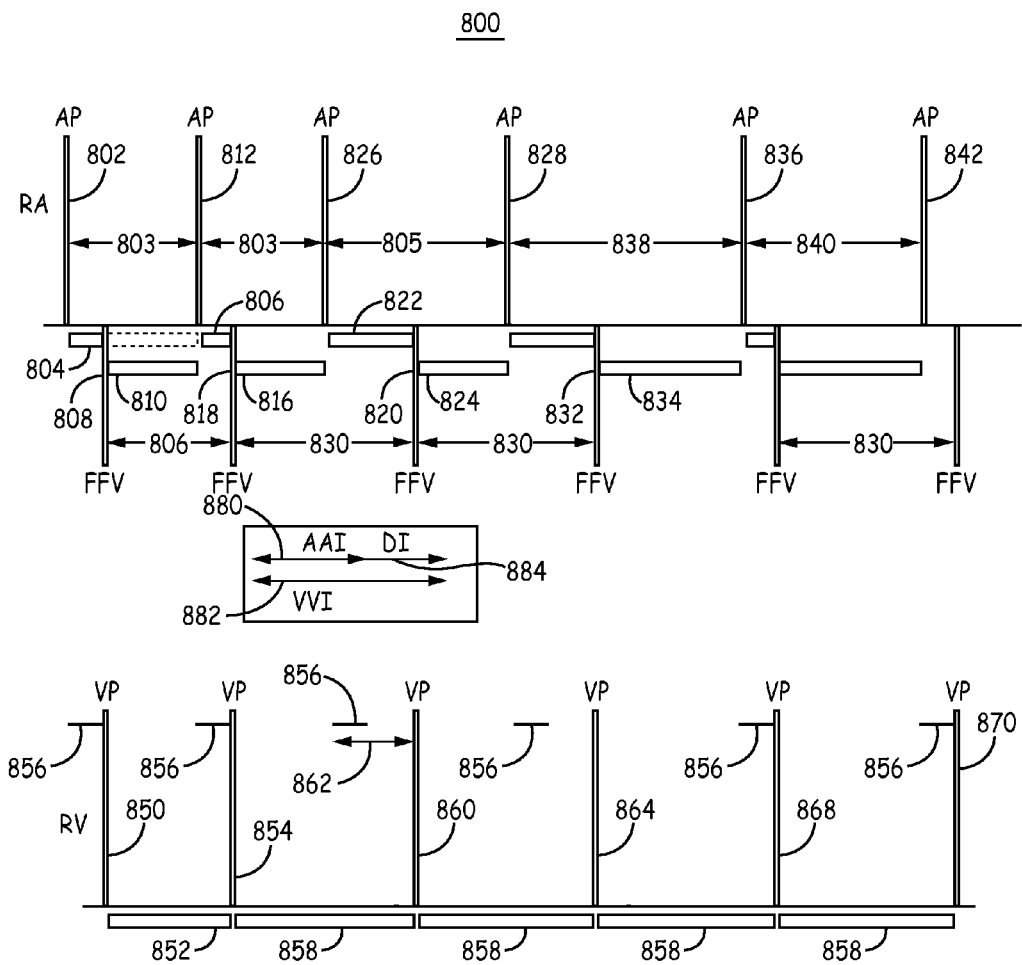

FIG. 9 is a timing diagram 800 illustrating atrial pacing pulses and ventricular pacing pulses delivered by RA pacemaker 12 and RV pacemaker 14, and the operation of RA pacemaker 12 when the atrial rate is determined to be faster than a FF ventricular event rate ("yes" branch of block 414 in flow chart of FIG. 7). Atrial pacing pulse 802 starts an AA escape interval 804 set equal to a previously established LRI 803. As described above, the LRI 803 may be established based on a sensor-indicated rate determined by the control module 206 of the RA pacemaker 12.

The atrial escape interval timer is restarted in response to a sensed FF ventricular event 808. The atrial escape interval 804 is reset to a VA escape interval 810 that is equal to the established LRI 803 less a target AV interval 856. The next atrial pacing pulse 812 is delivered upon expiration of the VA escape interval 810. The atrial escape interval timer is restarted to an AA escape interval 806 equal to the established LRI 803, which is again interrupted by a FF ventricular event 818 that restarts a VA escape interval 816. As long as the ventricular pacing rate does not change, atrial pacing pulses 802 and 812 are delivered at the target AV interval 856 prior to the ventricular pacing pulses 850 and 854.

If the ventricular pacing rate is decreased, however, e.g., when a new ventricular LRI is determined in response to the ventricular sensor-indicated rate, the atrial pacing pulses may fall out of range of the target AV interval 856. For example, a newly established ventricular LRI 858 that is longer than the previous ventricular escape interval 852 is set in response to ventricular pacing pulse 854. The next ventricular pacing pulse 860 occurs at an actual AV interval 862 that is much longer than the target AV interval 856 following atrial pacing pulse 826, because of a mismatch between the atrial sensor-indicated rate and the ventricular sensor-indicated rate.

The atrial escape interval timer is set to an AA escape interval 822, still equal to the previously established atrial LRI 803, in response to the atrial pacing pulse 826. A sensed FF ventricular event 820 associated with ventricular pacing pulse 860 occurs later in the AA escape interval 822 because the ventricular pacing rate has slowed. A VA escape interval 824 is set in response to the FF ventricular event 820 and is still based on the previously established atrial LRI 803, less the target AV interval 856. As a result, the atrial pacing pulse 828 delivered upon expiration of the VA escape interval 824 occurs at a long AA interval 805 due the relatively late FF ventricular event 820. Atrial pacing pulse 828 occurs prior to the next ventricular pacing pulse 864 at an actual AV interval that is much longer than the target AV interval 856.

The RA pacemaker 12, however, monitors the rate of the FF ventricular events 818, 820 and 832 and determines that the atrial LRI 803 needs to be increased to slow the atrial pacing rate to match the slower FF ventricular event rate, assuming the established atrial LRI 803 is not already at the programmed atrial base pacing rate interval. As illustrated in the center inset box, the control module 206 of RA pacemaker 12 may determine a difference interval 884 between a VV interval 882 determined from one or more FF ventricular event intervals 830 and the AA interval 880 equal to the current atrial LRI 803. The atrial LRI 803 may be increased by the difference interval 884 to slow the rate of atrial pacing pulses. The increase may be performed in one step or more gradually in multiple increments of the atrial LRI 803.

The next sensed FF ventricular event 832 causes the atrial pacing escape interval timer to be reset to a new VA escape interval 834 that is equal to the adjusted (increased) atrial LRI less the target AV interval 856. As a result, the next atrial pacing pulse 836 delivered upon expiration of VA escape interval 834 occurs at an extended AA interval 838 due to the increased VA escape interval 834 started relatively late in the atrial cycle upon sensing FF ventricular event 832. The atrial pacing pulse 836 is, however, delivered at the restored target AV interval 856 prior to the next ventricular pacing pulse 868.

By the next cardiac cycle, matching atrial and ventricular rates are also restored. Atrial pacing pulses 836 and 842 occur at the adjusted atrial LRI 840 that matches the FF ventricular event interval 830 equal to the ventricular LRI 858 between ventricular pacing pulses 868 and 870. By monitoring for a FF ventricular event rate that is slower than an atrial rate, the RA pacemaker 12 can quickly res-establish coordination between atrial pacing pulses and ventricular pacing pulses by adjusting the atrial LRI when the currently established atrial LRI is shorter than the base pacing rate interval.

Referring again to the flow chart 400 of FIG. 7, the operation of RA pacemaker 12 when the atrial and FF ventricular event rates are substantially equal will now be described. The negative result at both of blocks 404 and 414 indicates that the atrial and FF ventricular event rates match based on comparison between a determined AA interval and a determined FF ventricular event interval, both of which may be based on one or more respective atrial event intervals and FF ventricular event intervals. A match between the event rates may be detected when the interval measurements are within 10 ms of each other, 20 ms of each other or other predetermined matching range. If the AA and FF ventricular event interval comparison(s) indicate a match between the atrial and FF ventricular event rates, the actual AV interval is monitored at block 430.

In some circumstances, the atrial and ventricular rates may match, but the actual AV interval may be outside an acceptable range of the target AV interval. For example, a difference of a few milliseconds that is within the "matching range" may accumulate over time to shift the timing of atrial events outside the target AV interval relative to ventricular events. Normally, a sensed FF ventricular event will cause the atrial pacing escape interval to be set to a VA interval that will schedule the next atrial pacing pulse at the target AV interval earlier than the next expected ventricular event. However, in some instances, a ventricular event may occur very late in the atrial cycle. An example of this situation is shown in FIG. 10A.

Figure 10A:
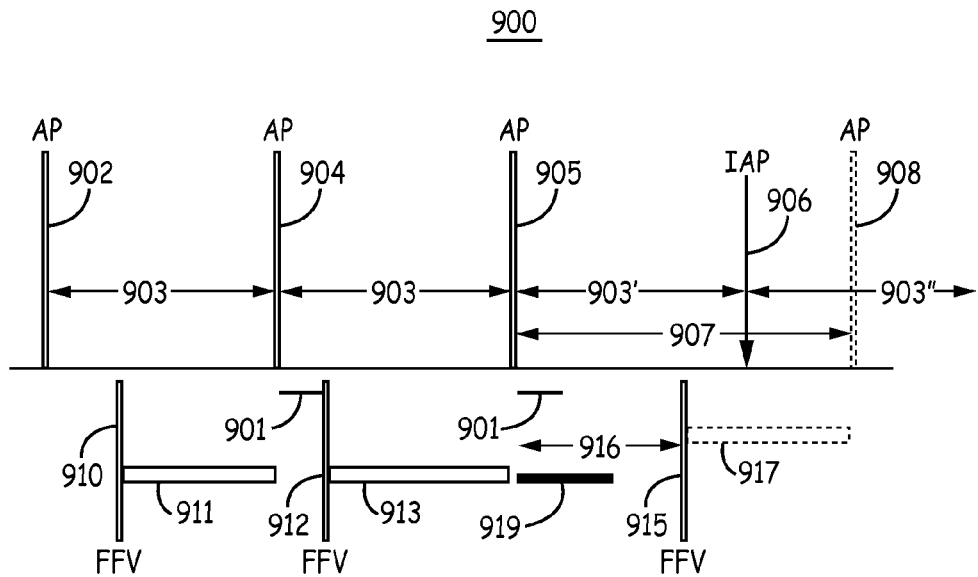

FIG. 10A is a timing diagram 900 illustrating atrial pacing pulses and sensed FF ventricular events. Atrial pacing pulses 902, 904 and 905 may each be delivered upon expiration of a respective VA escape interval 911, 913 set in response to a sensed FF ventricular event 910, 912. The VA escape intervals 911 and 913 are set to the established atrial LRI 903 less a target AV interval 901. However, if a FF ventricular event 915 is sensed late in the atrial cycle, e.g., at interval 916 following atrial pacing pulse 905, a VA escape interval 917 started late in the atrial cycle would lead to an atrial pacing pulse 908 delivered at an actual AA interval 907 that is much longer than the established atrial LRI interval 903. The late FF ventricular event 915 may be an over-sensed T-wave, a PVC, or electrical noise for example. In other instances, a late-occurring sensed FF ventricular event 915 may be a true ventricular event that has shifted later in the atrial cycle over multiple cardiac cycles due to a small difference in atrial and ventricular rate in the absence of AV conduction and in the absence of FF ventricular sensing by RA pacemaker 12 over multiple cycles.

The use of a VA escape interval in response to FF ventricular events as described previously in conjunction with FIG. 6 for controlling atrial pacing pulses may be limited in some examples based on the relative timing of the FF ventricular event. For instance, a VA escape interval may be set in response to sensing a FF ventricular event only if the FF ventricular event occurs within a VA time limit of the preceding atrial event. In the example shown in FIG. 10A, the actual AV interval 916 from the most recent atrial event 905 to the FF ventricular event 915 may be compared to a VA pacing limit 919. If the actual AV interval 916 after the most recent atrial event 905 is greater than a VA pacing limit 919, the FF ventricular event 915 may be ignored by the RA pacemaker control module 206 for the purposes of resetting the atrial pacing escape interval timer to VA escape interval 917.

In some examples, an AA interval set to the atrial LRI 903' at atrial pacing pulse 905 may be allowed to expire and an atrial pacing pulse (not shown) may be delivered at the expiration of the atrial LRI 903'. In other examples, the atrial LRI 903' is allowed to expire without delivering an atrial pacing pulse, (inhibited atrial pace, IAP 906. If an atrial pacing pulse is delivered at the expiration of atrial LRI 903', it may be conducted to the ventricles during ventricular repolarization following FF ventricular event 915. Ventricular tachycardia could potentially be induced in some instances. The atrial pacing pulse scheduled at the expiration of the atrial LRI 903' may, therefore, be withheld in response to the FF ventricular event 915 sensed during the LRI 903' outside a VA limit. The FF ventricular event 915 may or may not be used to set a VA interval. In some cases, the atrial LRI 903' is allowed to expire in response to the FF ventricular event 915 during the atrial LRI 903' but outside a VA limit, and a new atrial LRI 903" is started by the RA pacemaker control module 206 at the time of the IAP 906 to maintain regular AA intervals until an atrial pacing pulse is delivered or a FF ventricular event is sensed within a VA pacing limit 919.

A VA pacing limit 919 may be a time interval or percentage of the currently established atrial LRI or a time interval or percentage of the target AV interval. For example if the FF ventricular event 915 is at an actual AV interval 916 that is at least twice as long as the target AV interval 901, the sensed FF ventricular event 915 does not reset the atrial pacing escape interval to a VA interval. In another example, if the FF ventricular event 915 is sensed later than 30% of the atrial LRI 903', the atrial pacing escape interval is not reset to a VA interval in response to the FF ventricular event 915. The VA limit 919 may be applied to an actual AV interval 916 determined between a preceding atrial pacing pulse 905 and a sensed FF ventricular event 915 or between a preceding atrial sensed event and a sensed FF ventricular event for use in determining whether the VA interval 917 will be started in response to the sensed FF ventricular event 915 during an atrial pacing escape interval 903' started at the preceding atrial event 905, which is a paced event in this example but could be a sensed event.

Figure 10B:
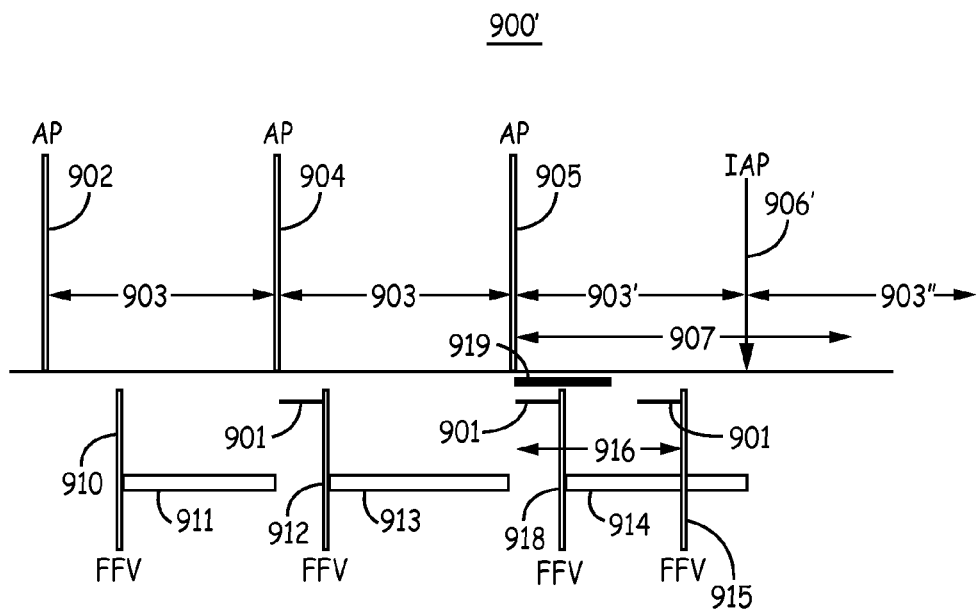

FIG. 10B is a timing diagram 900' illustrating atrial pacing pulses and sensed FF ventricular events as shown in FIG. 10A with the added FF ventricular event 918 sensed after atrial pacing pulse 905 at the targeted AV interval 901. FF ventricular event 918 may be a true FF ventricular event sensed prior to the late FF ventricular event 915, which may be an oversensed T-wave or premature ventricular contraction.

If a VA escape interval 914 is started in response to FF ventricular event 918 that arrived within the VA pacing limit 919, but a second FFV event 915 is sensed during the VA escape interval 914, the atrial pacing pulse scheduled at the expiration of the VA escape interval 914 may be inhibited (IAP 906') to avoid a conducted atrial evoked response from arriving during ventricular repolarization following FF ventricular event 915 when it is a PVC or true R-wave. A pacing pulse is not delivered but the scheduled time of the IAP 906' at the expiration of the VA escape interval 914 may be used to re-start the atrial pacing escape interval timer at an atrial LRI 903".

As indicated above, in some circumstances, a late-occurring FF ventricular event 915 may be a valid FF ventricular event, such as an event that has gradually shifted later in the atrial cardiac cycle. This situation could arise if FF ventricular event sensing is lost for a period of time, and the ventricular rate is slightly slower than the atrial rate. For example, if the atrial LRI is set to 900 ms and ventricular LRI is set to 910 ms, the rates would be determined to match if the matching range is ±10 ms or more. If FF ventricular event sensing is lost for an interval in time, the ventricular events will occur 10 ms later in each successive atrial cycle. When FF ventricular events are sensed within the VA limit, the VA escape interval will prevent a gradually increasing AV interval. However, if FF ventricular event sensing is lost for a few minutes, when sensing returns the FF ventricular event may be sensed later than the VA pacing limit 919. A one cycle adjustment based on setting a VA escape interval in response to the late-occurring sensed FF ventricular event 915 may be undesirable since it could result in a large step change in atrial rate. In this situation, therefore, more gradual changes to the atrial LRI 903 may be made to bring the atrial pacing pulses back into range of the target AV interval 901.

Referring again to flow chart 400 of FIG. 7, if the atrial rate and FF ventricular event rate are approximately equal ("no" branch of block 414), the RA pacemaker 12 determines the actual AV interval between an atrial event (paced or sensed) and a sensed FF ventricular event at block 430. The actual AV interval is compared to a VA pacing limit at block 432 that may be stored in RA pacemaker memory 210. If the actual AV interval is not greater than a VA pacing limit, as determined at block 432, no atrial LRI adjustment is made. VA pacing escape intervals are set by the control module 206 of RA pacemaker 12 in response to FF ventricular events to regulate the actual AV interval within range of the target AV interval. The process returns to block 402 to continue monitoring the atrial and FF ventricular event rates.

If the atrial rate and the FF ventricular event rate are approximately equal and the actual AV interval exceeds the VA pacing limit ("yes" branch of block 432), the RA pacemaker control module 206 adjusts the atrial LRI at block 435 to check for corresponding changes in the FF ventricular event rate as evidence of intrinsic AV conduction. If the late FF ventricular events are due to slow intrinsic AV conduction, adjustment of the atrial LRI will not correct the actual AV interval. Intrinsically conducted R-waves that are sensed as FF ventricular events will follow the atrial LRI changes at the same, long intrinsic AV conduction time. If the actual AV interval stays the same, AV block is not present as determined at block 436. No adjustments to the atrial LRI is made at block 438

If changes in the actual AV interval occur as the atrial rate is altered at block 435, the sensed FF ventricular events may be associated with ventricular pacing pulses being delivered by the RV pacemaker and therefore evidence of AV block. If AV block is detected at block 436 based on a change in the actual AV interval when the atrial rate is altered, the AA pacing escape interval is altered from the established atrial LRI at block 440 until the actual AV interval is within an acceptable range of the target AV interval. The established atrial LRI is not changed and atrial pacing resumes at the atrial LRI after restoring the target AV interval. The process returns to block 402 to continue monitoring the atrial and FF ventricular event rates for maintaining coordination between atrial pacing delivered by the RA pacemaker 12 and the RV pacemaker 14 operating independently of the RA pacemaker.

Figure 11:
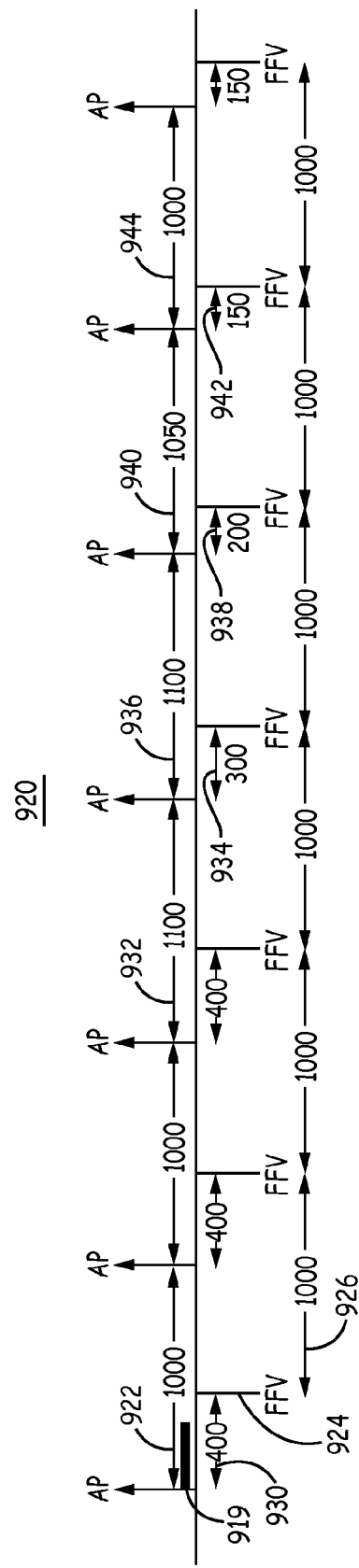

FIG. 11 is a timing diagram 920 illustrating the operation of the RA pacemaker 12 when the atrial rate and the FF ventricular rate have been determined to match ("no" branch of block 414 in FIG. 7). In this example, the atrial LRI 922 is 1000 ms corresponding to a base pacing rate of 60 beats per minute. The target AV interval is 150 ms. The ventricular LRI of the RV pacemaker 14 is also set to 1000 ms such that FF ventricular events (FFV) 924 are sensed by the RA pacemaker 12 at 1000 ms intervals 926. The FF ventricular events 924 are initially occurring late in the atrial cycle, at an actual AV interval 930 of 400 ms. The FF ventricular events 924 may arrive late in the atrial cardiac cycle due to gradual progression of a slightly slower ventricular pacing rate during a loss of FF ventricular sensing by the RA pacemaker 12. The FF ventricular events 924 may also be pacing pulses (or evoked R-waves) arriving late due to a VV escape interval being set in response to a previously oversensed T-wave or sensed premature ventricular contraction by the RV pacemaker 14.

The first FF ventricular events 924 occur at an actual AV interval 930 of 400 ms, greater than the target AV interval of 150 ms and greater than a VA pacing limit 919 of, e.g., twice the target AV interval. Accordingly, no VA escape interval is set in response to the FF ventricular events 924, and atrial pacing pulses (AP) continue at the 1000 ms LRI 922.

The RA pacemaker 12 determines that the AA intervals 922 and FFV intervals 926 match, but that the AV interval 930 is greater than the VA pacing limit 919. The atrial LRI is temporarily adjusted by a predetermined maximum step size of 100 ms in this example to a lengthened AA escape interval 932 of 1100 ms. The RA pacemaker control module 206 determines if the actual AV interval 934 has changed in response to the change in the AA escape interval 932. Since the actual AV escape interval 934 shortened by 100 ms (from 400 ms to 300 ms), intrinsic AV conduction is not intact. The FF ventricular event rate is independent of changes in the atrial rate and is likely a ventricular paced rate.

If the actual AV interval 934 had stayed unchanged at 400 ms, the long AV intervals would be attributed to slow intrinsic conduction and the atrial LRI of 1000 ms would be restored without further adjustment. Since AV conduction is not present, however, based on the change in the actual AV interval 300 in response to a change in the AA escape interval 932, and the ventricular rate is remaining stable at the ventricular paced rate of 60 bpm, the atrial pacing pulse timing can be adjusted to restore the target AV interval.

On the next atrial pacing cycle, the AA escape interval 936 is again lengthened from the atrial LRI 922 by the maximum step size of 100 ms to deliver the next atrial pacing pulse at another 1100 ms AA interval 936. The actual AV interval 938 is reduced from the original 400 ms AV interval 930 to 200 ms by stepping out the atrial pacing pulses 100 ms on each of two consecutive cycles. Since the target AV interval is 150 ms in this example, the next AA escape interval 940 is lengthened only 50 ms from the atrial LRI 922 of 1000 ms to an AA escape interval of 1050 ms. The next actual AV interval 942 is thereby reduced to 150 ms, the target AV interval. Since the target AV interval has been restored, the atrial LRI 944 can be resumed. Atrial pacing continues at a rate (1,000 ms AA interval) that matches the FF ventricular event rate with the atrial pacing pulses arriving at the target AV interval 942 ahead of the FF ventricular events (FFV).

In the example shown, the actual AV interval 930 is initially detected to be longer than the target AV interval 942. In other examples, the actual AV interval may initially be detected to be shorter than the target AV interval. If the atrial rate and FF ventricular event rate are equal, but the actual AV interval is too long or too short and AV conduction block is verified, the AA escape interval can be lengthened or shortened, respectively, for one or more cycles as demonstrated in FIG. 11 to change the timing of the atrial pacing pulses relative to the FF ventricular event to bring the atrial pacing pulses to a target AV interval. It is noted that when the AA escape interval is lengthened, an intrinsic atrial event could occur. As such, a maximum step size may be used to maintain control of the atrial rate by pacing.

In some examples, AV interval correction by AA escape interval adjustment is performed only when the actual AV interval deviates from the target AV interval by a threshold amount, e.g., more than 30 ms. In other examples, the AA escape interval could be adjusted on a beat-by-beat basis to shorten or lengthen an actual AV interval in smaller steps within a range of the target AV interval.

Figure 12:
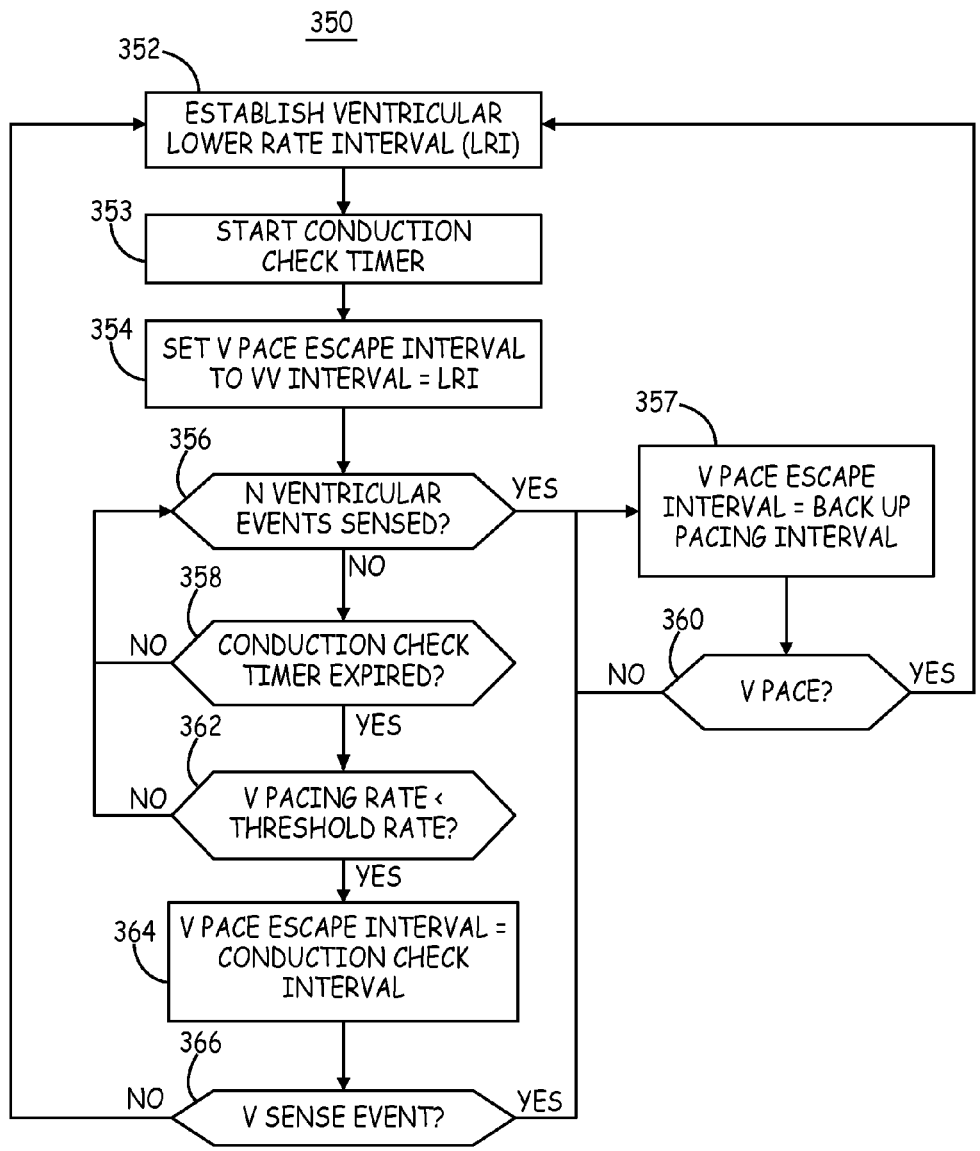
FIG. 12 is a flow chart of a method for controlling ventricular pacing pulses by a ventricular intracardiac pacemaker according to one example.

FIG. 12 is a flow chart 350 of a method for controlling ventricular pacing pulses by RV pacemaker 14 according to one example. RV pacemaker 14 may or may not be configured to sense FF atrial events. The methods described above performed by RA pacemaker 12 achieve coordinated atrial and ventricular pacing by the two separate intracardiac pacemakers without requiring RV pacemaker 14 to sense atrial events. In patients having intermittent AV block, it is desirable to minimize ventricular pacing in the presence of normal AV conduction. The RV pacemaker 14 may therefore be configured to provide only back-up pacing when intrinsically conducted ventricular events are sensed and periodically test for a return of AV conduction during episodes of sustained ventricular pacing.

At block 352, a ventricular LRI is established, which may be based on a physiological sensor signal indicative of the metabolic need of the patient. An escape interval timer included in the RV pacemaker control module is set to a W escape interval equal to the established LRI.

A conduction check timer is started at block 353. Expiration of the conduction check timer will cause the RV pacemaker 14 to perform an AV conduction check after a period of sustained ventricular pacing to ensure that the ventricular pacing is not masking a return of AV conduction. At block 354, the ventricular pacing escape interval is set to a VV interval equal to the established LRI. The ventricular LRI may be adjusted over time based on a sensor-indicated rate when rate responsive pacing is enabled. The ventricular LRI may be adjusted between a programmed base pacing rate interval and an interval corresponding to a maximum ventricular pacing rate.

If a threshold number of intrinsic ventricular events, e.g., at least one intrinsic event or at least two consecutive intrinsic events, are sensed by the sensing module 204 of RV pacemaker 14 at block 356, the control module 206 of RV pacemaker 14 sets the ventricular pacing escape interval to a back-up pacing interval at block 357.

The threshold number of intrinsic sensed events is evidence of normal intrinsic AV conduction. Ventricular pacing at the established LRI is inhibited and only back-up ventricular pacing is provided when AV conduction is intact. The back-up pacing interval may be the base pacing rate interval or another interval longer than an established ventricular LRI. The back-up pacing interval may be set to be a fixed interval longer than the base rate interval, a fixed interval longer than a sensor indicated rate interval, or a rate-dependent interval longer than the sensor-indicated rate interval. Back-up ventricular pacing is provided at the back-up interval if AV conduction block returns.

If one or more ventricular pacing pulses are delivered at the back-up pacing interval, as determined at block 360, AV block may be present. The process returns to block 352 to re-establish the ventricular LRI interval and restart the conduction check timer at block 353. The ventricular pacing escape interval is set to the LRI at block 354. If ventricular sensing does not occur at block 356, ventricular pacing at the LRI continues until sensing of intrinsic ventricular events (i.e., R-waves) occurs or the conduction check timer expires, as determined at block 358.

If the ventricular pacing rate is less than a threshold rate, as determined at block 362, a conduction check is performed at block 364. If the pacing rate exceeds a conduction check threshold rate, the conduction check is not performed or is performed but after the pacing rate drops below the conduction check threshold rate. The threshold rate compared to the ventricular pacing rate at block 362 may be less than 100 bpm, e.g., 80 bpm, so that a conduction check is performed when a patient is at rest or relatively low activity.

If the pacing rate is less than the threshold rate, the conduction check may be performed by setting the ventricular pacing escape interval to a conduction check interval that is longer than the current LRI at block 364. The conduction check interval may be set for one or more pacing cycles, for example up to five pacing cycles. The RV pacemaker 14 determines if a ventricular sense event occurs during the conduction check escape interval at block 366. If sensing does not occur, the RV pacemaker 14 continues pacing at the ventricular LRI. If an intrinsic event is sensed, i.e., an R-wave is sensed during the conduction check escape interval, the RV pacemaker 14 returns to block 357 to set the ventricular pacing escape interval to a back-up pacing interval. In this way, the RV pacemaker 14 is not required to sense atrial events in order to control ventricular pacing in a manner that inhibits ventricular pacing when AV conduction is intact and enables ventricular pacing when AV conduction block is present.

Thus, various examples of an implantable medical device system for delivering coordinated atrial and ventricular pacing using separate intracardiac pacemakers have been described according to illustrative embodiments. However, various modifications may be made to the described embodiments without departing from the scope of the following claims.

The invention claimed is:

1. An implantable cardiac pacing system, comprising:
a first pacemaker implantable in a first chamber of a heart of a patient and comprising:
a first sensing module configured to receive a cardiac electrical signal and sense near field events in the first chamber from the cardiac electrical signal,
a first pulse generator configured to generate and deliver pacing pulses to the first chamber via a pair of electrodes, and
a first control module coupled to the first sensing module and the first pulse generator and configured to:
establish a lower rate interval to control a rate of delivery of the pacing pulses,
schedule a first pacing pulse to be delivered by the first pulse generator by starting a first pacing escape interval equal to the lower rate interval,
withhold the scheduled first pacing pulse in response to the first sensing module sensing a near-field event during the first pacing escape interval, and
schedule a next pacing pulse to be delivered at the lower rate interval from a time that the first pacing escape interval is scheduled to expire.

2. The system of claim 1, wherein the first control module is configured to schedule the next pacing pulse by:
starting a second pacing escape interval at a time that the near-field event is sensed by the sensing module during the first pacing escape interval, the second pacing escape interval comprising a sum of the lower rate interval and an unexpired portion of the first pacing escape interval at the time that the near-field event is sensed during the first pacing escape interval.

3. The system of claim 1, wherein the first control module is configured to schedule the next pacing pulse by:
allowing the first pacing escape interval to expire; and
starting a second pacing escape interval equal to the lower rate interval upon expiration of the first pacing escape interval.

4. The system of claim 3, wherein the first control module is further configured to:
withhold the next pacing pulse at an expiration of the second pacing escape interval in response to the first sensing module sensing a near-field event during the second pacing escape interval; and
start a third pacing escape interval equal to the lower rate interval upon expiration of the second pacing interval.

5. The system of claim 1, wherein:
the first sensing module is further configured to sense far field events, the far-field event occurring in a second chamber of the heart different than the first chamber; and
the first control module further configured to schedule the next pacing pulse by starting a second pacing escape interval equal to the lower rate interval less a target inter-chamber interval in response to the first sensing module sensing a far field event during the first escape interval.

6. The system of claim 5, wherein the first control module is further configured to:
withhold the next pacing pulse scheduled to be delivered at an expiration of the second pacing escape interval in response to the first sensing module sensing a near-field event at a time during the second pacing escape interval; and
schedule a third pacing pulse to be delivered to the first chamber at the lower rate interval from the expiration of the second pacing escape interval.

7. The system of claim 6 wherein the first control module is configured to schedule the third pacing pulse by:
starting a third pacing escape interval in response to the first sensing module sensing the near-field event at a time during the second pacing escape interval, the third pacing escape interval comprising a sum of the lower rate interval and an unexpired time of the second pacing escape interval remaining at the time that the near-field event was sensed during the second pacing escape interval.

8. The system of claim 6 wherein the first control module is configured to schedule the third pacing pulse by:
allowing the second pacing escape interval to expire; and
starting a third pacing escape interval equal to the lower rate interval upon expiration of the second pacing escape interval.

9. The system of claim 5, wherein the first control module is further configured to:
determine a time interval from a preceding event in the first chamber to the sensed far-field event;
compare the determined time interval to a time limit; and
start the second pacing escape interval only if the determined time interval is within the time limit.

10. The system of claim 9, wherein the first control module is further configured to:
allow the first pacing escape interval to expire in response to the determined time interval being outside the time limit;
withhold the first scheduled pacing pulse upon expiration of the first pacing escape interval; and
start a third pacing escape interval equal to the lower rate interval upon expiration of the first pacing escape interval.

11. The system of claim 5, wherein the first control module is further configured to:
allow the second pacing escape interval to expire in response to the sensing module sensing a next far-field event during the second pacing escape interval;
withhold a pacing pulse scheduled to occur at the expiration of the second pacing escape interval; and
start a third pacing escape interval equal to the lower rate interval at the expiration of the second pacing escape interval.

12. The system of claim 5, further comprising an acoustical sensor configured to produce a signal comprising heart sounds signals;
the first sensing module configured to sense the far field ventricular events from the acoustical sensor signal.

13. The system of claim 1, further comprising:
a second pacemaker implantable in a second chamber of the heart of the patient and comprising:
a second sensing module configured to receive a second cardiac electrical signal and sense second chamber near field events from the second cardiac electrical signal, the second chamber near field events occurring in the second chamber,
a second pulse generator configured to generate and deliver pacing pulses to the second chamber via a second pair of electrodes, and
a second control module configured to:
establish a second lower rate interval for controlling a rate of the pacing pulses delivered to the second chamber;
set a second chamber pacing escape interval to a test interval longer than the second lower rate interval in response to the second sensing module sensing a second chamber near-field event during at least one second lower rate interval;
set the second chamber pacing escape interval to a back-up pacing interval longer than the second lower rate interval in response to the second sensing module sensing a second chamber near-field event during the test interval, and
set the second chamber pacing escape interval equal to the second lower rate interval in response to at least one back-up pacing interval expiring without the second sensing module sensing a second chamber near-field event during the at least one back-up pacing interval.

14. The system of claim 1, wherein the first intracardiac pacemaker comprises a housing enclosing the first sensing module, the first pulse generator, and the first control module, the pair of electrodes carried by the housing.

15. A method, comprising:
sensing near field events in a first chamber of a patient's heart from a cardiac electrical signal received by a first sensing module of a first pacemaker implantable in the first chamber;
establishing by the first pacemaker a lower rate interval to control a rate of delivery of pacing pulses;
scheduling a first pacing pulse by starting a first pacing escape interval set equal to the lower rate interval;
withholding the scheduled first pacing pulse in response to sensing a near-field event during the first pacing escape interval; and
scheduling a next pacing pulse to be delivered at the lower rate interval from a time that the first pacing escape interval is scheduled to expire.

16. The method of claim 15, further comprising:
starting a second pacing escape interval at a time that the near-field event is sensed by the sensing module during the first pacing escape interval, the second pacing escape interval comprising a sum of the lower rate interval and an unexpired portion of the first pacing escape interval at the time that the near-field event is sensed during the first pacing escape interval.

17. The method of claim 15, wherein scheduling the next pacing pulse comprises:
allowing the first pacing escape interval to expire; and
starting a second pacing escape interval equal to the lower rate interval upon expiration of the first pacing escape interval.

18. The method of claim 17, further comprising:
withholding the next pacing pulse at an expiration of the second pacing escape interval in response to the first sensing module sensing a near-field event during the second pacing escape interval; and
starting a third pacing escape interval equal to the lower rate interval upon expiration of the second pacing interval.

19. The method of claim 15, further comprising:
sensing far field events by the first pacemaker, the far field events occurring in a second chamber of the heart different than the first chamber; and
scheduling the next pacing pulse by starting a second pacing escape interval equal to the lower rate interval less a target inter-chamber interval in response to the first sensing module sensing a far field event during the first escape interval.

20. The method of claim 19, further comprising:
withholding the next pacing pulse scheduled to be delivered at an expiration of the second pacing escape interval in response to sensing a near-field event at a time during the second pacing escape interval; and
scheduling a third pacing pulse to be delivered to the first chamber at the lower rate interval from the expiration of the second pacing escape interval.

21. The method of claim 20, wherein scheduling the third pacing pulse comprises:
starting a third pacing escape interval in response to sensing the near-field event at a time during the second pacing escape interval, the third pacing escape interval comprising a sum of the lower rate interval and an unexpired time of the second pacing escape interval remaining at the time that the near-field event was sensed during the second pacing escape interval.

22. The method of claim 20, wherein scheduling the third pacing pulse comprises:
allowing the second pacing escape interval to expire; and
starting a third pacing escape interval equal to the lower rate interval upon expiration of the second pacing escape interval.

23. The method of claim 19, further comprising:
determining a time interval from a preceding event in the first chamber to the sensed far-field event;
comparing the determined time interval to a time limit; and
starting the second pacing escape interval only if the determined time interval is within the time limit.

24. The method of claim 23, further comprising:
allowing the first pacing escape interval to expire in response to the determined time interval being outside the time limit;
withholding the first scheduled pacing pulse upon expiration of the first pacing escape interval; and
starting a third pacing escape interval equal to the lower rate interval upon expiration of the first pacing escape interval.

25. The method of claim 19, further comprising:
allowing the second pacing escape interval to expire in response to the sensing module sensing a next far-field event during the second pacing escape interval;
withholding a pacing pulse scheduled to occur at the expiration of the second pacing escape interval; and
starting a third pacing escape interval equal to the lower rate interval at the expiration of the second pacing escape interval.

26. The method of claim 15, further comprising:
sensing second chamber near field events by a second sensing module of a second pacemaker implantable in a second chamber of the patient's heart different than the first chamber, the second chamber near field events occurring in the second chamber,
establishing by the second pacemaker a second lower rate interval for controlling a rate of the pacing pulses delivered to the second chamber;
setting by the second pacemaker a second chamber pacing escape interval to a test interval longer than the second lower rate interval in response to the second sensing module sensing a second chamber near-field event during at least one second lower rate interval;
setting the second chamber pacing escape interval to a back-up pacing interval longer than the second lower rate interval in response to the second sensing module sensing a second chamber near-field event during the test interval, and
setting the second chamber pacing escape interval equal to the second lower rate interval in response to at least one back-up pacing interval expiring without the second sensing module sensing a second chamber near-field event during the at least one back-up pacing interval.

27. The method of claim 19, further comprising sensing the far field ventricular events from an acoustical sensor signal.

28. A non-transitory, computer-readable medium comprising a set of instructions which, when executed by a control module of a pacemaker implantable in a chamber of a patient's heart, cause the pacemaker to:
sense near field events from a cardiac electrical signal;
establish a lower rate interval to control a rate of delivery of pacing pulses;
schedule a first pacing pulse by starting a pacing escape interval set equal to the lower rate interval;
withholding the scheduled first pacing pulse in response to sensing a near-field event during the pacing escape interval; and
scheduling a next pacing pulse to be delivered at the lower rate interval from a time that the pacing escape interval is scheduled to expire.

\* \* \* \* \*